(12) United States Patent
Zavoronkovs et al.

(10) Patent No.: US 12,040,057 B2
(45) Date of Patent: Jul. 16, 2024

(54) SCAFFOLD-ORIENTED UNIVERSAL LINE SYSTEM

(71) Applicant: INSILICO MEDICINE IP LIMITED

(72) Inventors: Aleksandrs Zavoronkovs, Pak Shek Kok (HK); Daniil Polykovskiy, Moscow (RU); Maksim Kuznetsov, Moscow (RU); Andrey Filimonov, Moscow (RU)

(73) Assignee: INSILICO MEDICINE IP LIMITED, Hong Kong (HK)

( * ) Notice: Subject to any disclaimer, the term of this patent is extended or adjusted under 35 U.S.C. 154(b) by 1148 days.

(21) Appl. No.: 16/831,747

(22) Filed: Mar. 26, 2020

(65) Prior Publication Data

US 2021/0233621 A1    Jul. 29, 2021

Related U.S. Application Data

(60) Provisional application No. 62/966,465, filed on Jan. 27, 2020.

(51) Int. Cl.
| | | |
|---|---|---|
| *G01N 33/48* | (2006.01) | |
| *G01N 33/50* | (2006.01) | |
| *G09B 23/20* | (2006.01) | |
| *G09B 23/24* | (2006.01) | |
| *G16C 20/80* | (2019.01) | |
| *G16C 20/90* | (2019.01) | |

(52) U.S. Cl.
CPC ............. *G16C 20/80* (2019.02); *G09B 23/20* (2013.01); *G09B 23/24* (2013.01); *G16C 20/90* (2019.02)

(58) Field of Classification Search
CPC ........ G16C 20/80; G16C 20/90; G09B 23/20; G09B 23/24
See application file for complete search history.

(56) References Cited

U.S. PATENT DOCUMENTS

| 11,403,521 B2 | 8/2022 | Aliper et al. |
| 2020/0082916 A1 | 3/2020 | Polykovskiy et al. |
| 2020/0090049 A1 | 3/2020 | Aliper et al. |

OTHER PUBLICATIONS

Honda et al. SMILES transformer: Pre-trained molecular fingerprint for low data drug discovery. arXiv:1911.04738v1, Nov. 12, 2019, 9 pages.*
International Search Report and Written Opinion for PCTIB2021050273 mailed Mar. 23, 2021.

(Continued)

*Primary Examiner* — Russell S Negin
(74) *Attorney, Agent, or Firm* — MASCHOFF BRENNAN

(57) ABSTRACT

A scaffold-oriented line notation can include: a scaffold sequence of atom identifiers of a scaffold, the scaffold sequence includes at least one decoration marker or any number of decoration markers, each decoration marker being adjacent to an atom identifier of a linking atom of the scaffold; a decoration separator following a last atom identifier or a last decoration marker of the scaffold sequence; at least one decoration having at least one atom identifier in a line notation that defines a chemical structure of the chemical moiety of the decoration that is attached to the linking atom of the scaffold of the molecule; in the scaffold sequence, an order of the at least one decoration marker defines an order of the at least one decoration; in the at least one decoration, the first decoration follows the first decoration separator.

36 Claims, 11 Drawing Sheets

(56) References Cited

OTHER PUBLICATIONS

Noel M O'Boyle et al: "Open Babel: An open chemical toolbox", Journal of Cheminformatics, Biomed Central Ltd, London, UK, vol. 3, No. 1, Oct. 7, 2011 (Oct. 7, 2011), p. 33, XP021111311, ISSN: 1758-2946, DOI: 10.1186/1758-2946-3-33.

Warr Wendy A.: "Representation of chemical structures", Wiley Interdisciplinary Reviews: Computational Molecular Science, vol. 1, No. 4, Mar. 30, 2011 (Mar. 30, 2011), pp. 557-579, KP055783780, ISSN: 1759-0876, DOI: 10.1002/wcms.36.

Mario Krenn et al: "SELFIES: a robust representation of semantically constrained graphs with an example application in chemistry", arxiv.org, Cornell University Library, 201 Olin Library Cornell University Ithaca, NY 14853, May 31, 2019 (May 31, 2019).

Boyle Noel O et al: "DeepSMILES: An Adaptation of SMILES for Use in Machine-Learning of Chemical Structures", Sep. 19, 2018 (Sep. 19, 2018), XP055784369, DOI: 10.26434/chemrxiv.7097960. v1 Retrieved from the Internet: URL:https://chemrxiv.org/ndownloader/files/13059146 [retrieved on Mar. 10, 2021].

Arus-Pous, Josep; Patronov, Atanas; Bjerrum, Esben Jannik; Tyrchan, Christian; Reymond, Jean-Louis; Chen, Hongming; et al. (2020): SMILES-Based Deep Generative Scaffold Decorator for De-Novo Drug Design. ChemRxiv. Preprint. https://doi.org/10.26434/chemrxiv.11638383.v1.

\* cited by examiner

SCAFFOLD-ORIENTED UNIVERSAL LINE SYSTEM

CROSS-REFERENCE

This patent application claims priority to U.S. Provisional Application No. 62/966,465 filed Jan. 27, 2020, which provisional is incorporated herein by specific reference in its entirety.

BACKGROUND

Field

The present disclosure relates to systems and methods that provide a scaffold-oriented universal line system for chemical notations. More particularly, the present disclosure relates to systems and methods for converting a simplified molecular-input line-entry system (SMILES) notation or graph notation of a molecule to a more useful scaffold-oriented universal line system (SOULS).

Description of Related Art

Chemical structures have at least a two-dimensional graphical representation of a molecule, and often a three-dimensional representation of the molecule. However, such 2D or 3D representations are difficult to use during computing the chemical structures in computer environments. As such, the chemical structures can be defined in a line notation, such as a molecular string representation. The molecular string representation is a line notation for describing the structure of chemical species using ASCII strings. An example of such a representation is a simplified molecular-input line-entry system (SMILES). The SMILES representation can be obtained from analysis of the chemical structure of a molecule, and the SMILES representation can be converted back to the 2D or 3D chemical structure. Other molecular linear notations include the Wiswesser line notation (WLN), ROSDAL, and SYBYL Line Notation (SLN).

Thus, there is a need for a line notation for chemical structures that can be used in computing protocols. While some line notations are currently available, computing technologies continue to be updated and improved. The development of deep neural networks (DNNs) continues to drive the optimization and improvement of data processing. These DNNs have been configured to generate objects that satisfy defined conditions. For example, the DNNs can generate a molecule that has a specific biological activity for a specific target (e.g., receptor involved in disease state). Therefore, there continues to be a need for improving line notations of chemical structures for computing technologies.

SUMMARY

In some embodiments, a scaffold-oriented line notation for a chemical structure can include: a scaffold sequence of a plurality of atom identifiers arranged in a line notation that defines a scaffold of a chemical structure of a molecule, wherein the scaffold sequence includes at least one decoration marker (or any number of decoration markers), each decoration marker being adjacent to an atom identifier of a linking atom of the scaffold that is linked to a decoration, wherein in the chemical structure of the molecule the decoration is a chemical moiety that is bonded to the linking atom of the scaffold; a decoration separator following a last atom identifier or a last decoration marker of the scaffold sequence; at least one decoration (or any number of decorations) having at least one atom identifier in a line notation that defines a chemical structure of the chemical moiety of the decoration that is attached to the linking atom of the scaffold of the molecule; wherein: in the scaffold sequence, an order of the at least one decoration marker (or any number of decoration markers) defines an order of the at least one decoration (or any number of decorations); in the at least one decoration, the first decoration follows the first decoration separator; and in the at least one decoration, the first decoration is defined as being attached to a first linking atom identifier in the plurality of atom identifiers between a first atom identifier and the last atom identifier. While the scaffold-oriented line notation is described for molecules that include a scaffold and at least one decoration, it should be recognized that the scaffold-oriented line notation can be applied to molecules without any decorations. For example, benzene can be represented by the scaffold-oriented line notation and it does not have any decorations.

In some embodiments, the at least one decoration marker is located at one of: preceding a first atom identifier of the scaffold sequence that is bonded to a first decoration; following the first atom identifier of the scaffold sequence that is bonded to the first decoration; preceding a first linking atom identifier of the scaffold sequence that is bonded to a first decoration, wherein the first linking atom identifier is not the first atom identifier in the scaffold sequence; following the first linking atom identifier of the scaffold sequence that is bonded to the first decoration; preceding a subsequent atom identifier of the scaffold sequence that is bonded to the first decoration; or following the subsequent atom identifier of the scaffold sequence that is bonded to the first decoration.

In some embodiments, in the scaffold sequence, a first linking atom identifier of the plurality of atom identifiers is adjacent to a first decoration marker. In some aspects, the first decoration marker precedes the first atom identifier of the scaffold sequence. The first linking atom can be any atom including the first atom or last atom or any atom therebetween in the scaffold sequence.

In some embodiments, the line notation can include: at least a subsequent decoration marker adjacent with the subsequent atom identifier; at least a subsequent decoration separator following the first decoration; and at least a subsequent decoration following the at least one subsequent decoration separator, wherein each subsequent decoration is separated by a subsequent decoration marker.

In some embodiments, the line notation can include: a plurality of decoration markers adjacent with the corresponding atom identifier; a plurality of decorations separated by a plurality of decoration separators; and each of the plurality of decorations following a corresponding decoration separator. In some aspects, each decoration includes a corresponding decoration marker followed by a line notation of the chemical structure of the decoration. In some aspects, each atom identifier is defined by the periodic table. In some aspects, each decoration marker is a symbol. In some aspects, each decoration separator is a second symbol different from the decoration maker symbol. In some aspects, each decoration marker in the scaffold sequence is bound by a third symbol that is different from the decoration maker symbol and the decoration separator symbol.

In some embodiments, a method of converting a line notation of a chemical structure of a molecule to a scaffold-oriented line notation for the chemical structure can include: providing a line notation of the chemical structure; converting the line notation to a graph notation of the chemical structure; identifying a scaffold of the graph notation of the chemical structure; searching for at least one decoration of the graph notation of the chemical structure; separating the scaffold from any decoration; converting a graph representation of the scaffold to a corresponding line notation representation of the scaffold, wherein the line notation includes a plurality of atom identifiers arranged in a scaffold sequence; converting a graph representation of any decoration to a corresponding line notation representation of each decoration; identify a first linking atom in the scaffold attached to a first decoration, when a first decoration is present and linked to the first linking atom in the chemical structure; identifying a first linking atom identifier of the first linking atom in the scaffold sequence when the first linking atom is identified; placing a first decoration marker adjacent to the first linking atom identifier in the scaffold sequence, when the first decoration is present in the chemical structure; placing a first decoration separator following the last atom identifier or the last decoration marker of the scaffold sequence; placing the first decoration following the first decoration separator, when the first decoration is present in the chemical structure; and providing the scaffold-oriented line notation for the chemical structure. This method can be performed with molecules that includes a scaffold with or without decorations. When the molecule is only a scaffold, the method steps reciting actions with decorations are omitted.

In some embodiments, the method can include: identifying at least one decoration of the graph notation of the chemical structure; separating the scaffold from the at least one decoration; converting a graph representation of each decoration to a corresponding line notation representation of each decoration; identify the first linking atom identifier in the scaffold sequence for the first linking atom attached to the first decoration of the identified at last one decoration; placing the first decoration marker adjacent to the first linking atom identifier; placing the first decoration following the first decoration separator; and providing the scaffold-oriented line notation for the chemical structure, wherein the scaffold-oriented line notation includes the scaffold sequence and a decoration sequence of the at least one decoration, wherein the scaffold sequence and decoration sequence are separated by the first decoration separator.

In some embodiments, the method can include: identifying each atom and each bond of the chemical structure of the molecule; identifying the scaffold of the chemical structure; identifying each decoration that is attached to an atom of the scaffold; identifying each bond between each decoration and corresponding atom of the scaffold; and breaking the identified bond between each decoration and corresponding atom of the scaffold.

In some embodiments, the method can include: replacing each broken bond with a scaffold node linked to the corresponding atom of the scaffold; and replacing each broken bond with a decoration node lined to each decoration.

In some embodiments, the method can include: constructing a line notation of the scaffold having a decoration marker for each decoration node; and constructing a line notation of each decoration.

In some embodiments, the method can include: determining an order of the at least one decoration marker in the line notation of the scaffold; and arranging the at least one decoration in a decoration sequence having the order of the at least one decoration marker in the line notation of the scaffold, wherein each decoration has the decoration line notation and is separated by a decoration separator.

In some embodiments, the method can include: arranging the scaffold sequence so that the first decoration marker precedes the first linking atom identifier of the scaffold sequence. The first linking atom can be any atom including the first atom or last atom or any atom therebetween in the scaffold sequence.

In some embodiments, the method can include arranging the line notation to have: at least a subsequent decoration marker adjacent with the subsequent atom identifier; at least a subsequent decoration separator following the first decoration; and at least a subsequent decoration following the at least one subsequent decoration separator, wherein each subsequent decoration is separated by a subsequent decoration marker.

In some embodiments, the method can include arranging the line notation to have: a plurality of decoration markers adjacent with the corresponding atom identifier; a plurality of decoration separators separated by a plurality of decorations; and each of the plurality of decorations following a corresponding decoration separator.

In some embodiment, the method can include defining each decoration to include a corresponding decoration marker followed by a line notation of the chemical structure of the decoration.

In some embodiments, the scaffold-oriented line notation can include at least one of: each atom identifier is defined by the periodic table; each decoration marker is a symbol; each decoration separator is a second symbol different from the decoration maker symbol; or each decoration marker in the scaffold sequence is bound by a third symbol that is different from the decoration maker symbol and the decoration separator symbol.

In some aspects, a method of converting the scaffold-oriented line notation for the chemical structure of one of the embodiments to a different line notation of the chemical structure can include: providing the scaffold-oriented line notation for the chemical structure; splitting the scaffold-oriented line notation into the scaffold sequence and each decoration; constructing a graph representation of the scaffold sequence; constructing a graph representation of each decoration; combining the graph representation of the scaffold sequence and graph representation of each decoration to form a graph representation of the molecule; and converting the graph representation of the molecule to the different line notation. In some aspects, this method can include identifying a scaffold attachment point on the graph representation of the scaffold for each decoration; identifying the scaffold atom attached to scaffold attachment point for each decoration; and removing each scaffold attachment point. In some aspects, this method can include: identifying a decoration attachment point on the graph representation of each decoration; identifying a decoration atom attached to the decoration attachment point for each decoration; and removing each decoration attachment point.

In some embodiments, the method can include: connecting each scaffold atom with the corresponding decoration atom with a bond; and providing the graph representation of the chemical structure of the molecule.

In some embodiments, the method can include identifying a first decoration separator and each decoration separator between each decoration, the first decoration separator following the last atom identifier or last decoration marker.

In some embodiments, the method can include: identifying atom A in the scaffold defining an attachment point to a decoration; identifying atom B in a decoration defining an attachment point to the scaffold; identifying atom A_neig bonded to atom A; identifying atom B_neig bonded to atom B; removing atom A; removing atom B; and connecting atom A_neig by a bond to atom B_neig.

In some embodiments, the method can include: identifying each atom A in the scaffold defining an attachment point to a decoration; identifying each atom B in each decoration defining an attachment point to the scaffold; identifying each atom A_neig bonded to each atom A; identifying each atom B_neig bonded to atom each B; removing each atom A; removing each atom B; and connecting each atom A_neig by a bond to each corresponding atom B_neig.

In some embodiments, a method of computing a chemical structure can include: providing the scaffold-oriented line notation for the chemical structure of one of the embodiments into a computing system; and performing a computation protocol with the scaffold-oriented line notation with the computing system.

In some embodiments, a method of computing a chemical structure can include: providing the scaffold-oriented line notation for the chemical structure obtained by performing the method of one of the embodiments into a computing system; and performing a computation protocol with the scaffold-oriented line notation with the computing system.

In some aspects, a computer program product can include a non-transient, tangible memory device having computer-executable instructions that when executed by a processor, cause performance of the method of one of the embodiments for converting a line notation to the scaffold-oriented line notation.

In some aspects, computer program product can include a non-transient, tangible memory device having computer-executable instructions that when executed by a processor, cause performance of the method of converting the scaffold-oriented line notation to a different line notation.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

Figure 1A:
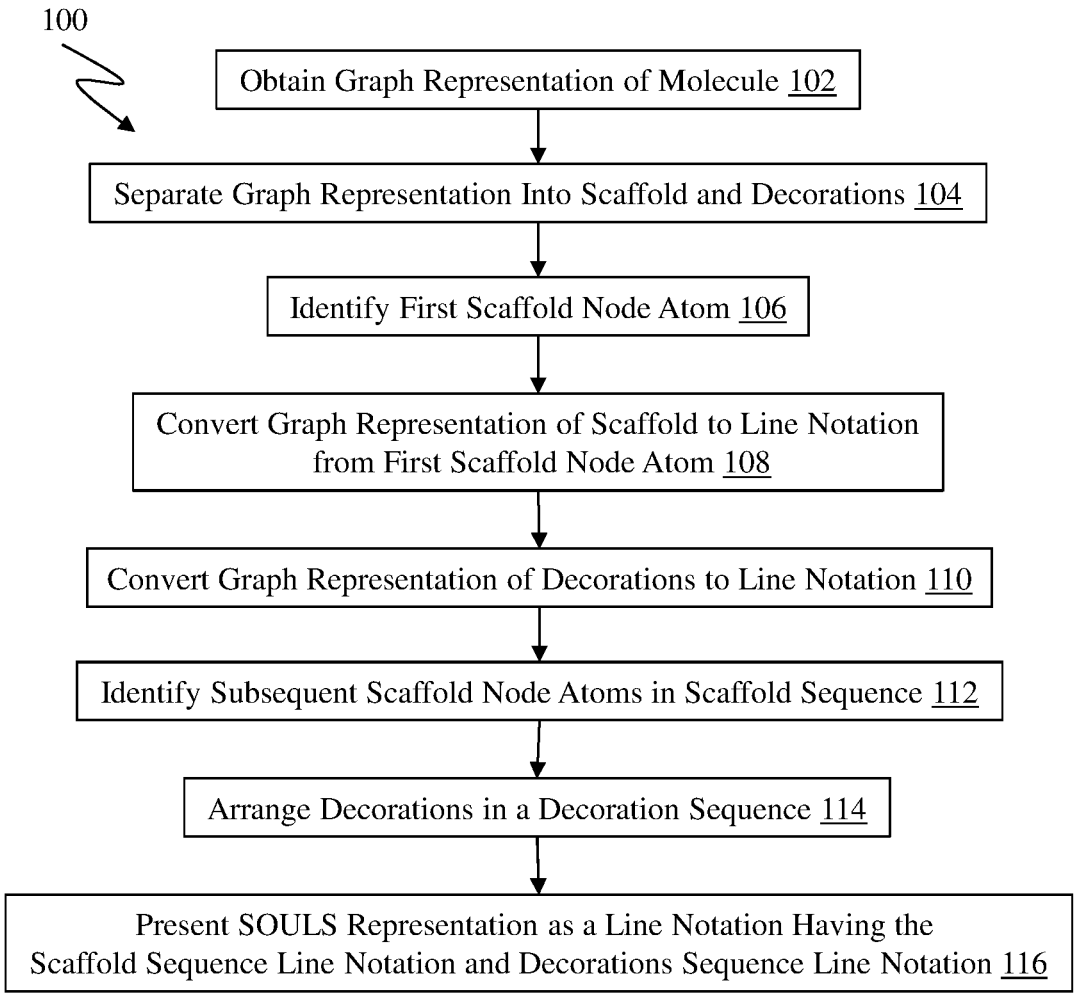
FIG. 1A illustrates a method of obtaining a SOULS representation.

The elements and components in the figures can be arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology includes systems and methods that provide a scaffold-oriented universal line system for chemical notations. More particularly, the present disclosure relates to systems and methods for converting a simplified molecular-input line-entry system (SMILES) to a useful scaffold-oriented universal line system (SOULS). However, it should be recognized that the systems and methods can be used to convert any chemical linear notation or graph notation into the SOULS notation that represents a chemical structure.

The SOULS representation of the chemical structure can be used in various computational technologies related to chemical structures. Some exemplary technologies that can be implemented with the SOULS representation are provided in the incorporated references. The SOULS representation can be particularly useful in artificial intelligence (AI), such as in training and using machine learning models for chemical analysis and design, as well as other computations that involve chemical structures or molecular data.

In some embodiments, the SOULS representation can be used to train a machine learning model. Accordingly, the SOULS representation represents molecular structures in a computer-readable format that can be processed by a computer during machine learning. The SOULS representation provides a scaffold-oriented representation of molecules that isolates a molecular scaffold from periphery chemical moieties (e.g., decorations) in the molecular representation. The SOULS representation is a chemical representation that is a useful tool for many machine learning approaches, including generative modeling, properties optimization using algorithms and reinforcement learning, and predictive modeling, as well as others.

In some embodiments, the systems and methods include an algorithm for converting a molecular structure into a SOULS representation. Accordingly, the system can include a computer that is configured with an algorithm that is designed to convert a any representation of a molecule into the SOULS representation. The system can obtain a molecular representation in various formats, such as string formats (e.g., line notations, linear formats, etc.) or graph representations. When the molecular representation is provided in a string format, the system uses a string to graph conversion to convert the string notation into a graph notation, which graph notation is then processed by the system to obtain the SOULS representation. When the molecular representation is provided in a graph notation, the graph notation is processed by the system to obtain the SOULS representation. Accordingly, the system can select the algorithms for obtaining the SOULS representation based on the format of the molecular structure that is provided.

In some embodiments, the system and method includes an algorithm for converting a molecular structure represented in the SOULS representation into other standard representations such as string formats (e.g., SMILES) or graphs (e.g., 2D or 3D). Accordingly, the system can include a computer that is configured with an algorithm that is designed to convert the SOULS representation into any other molecular representation, such as those recited herein. The conversion can continue across one or more steps until the desired representation is obtained.

In some embodiments, the conversion from the SOULS representation to another molecular representation can be used to provide a certain molecular representation that may be required for other defined operations. The ability to convert a molecular representation into the SOULS representation and then from SOULS back a molecular representation (e.g., non-SOULS) allows for two way chemical structure conversions between different variations, where molecular notations can be converted into SOULS representations and then converted back to the original notation or a different notation. Such one way or two way conversions can be used in various computational processing of chemical structure data.

In some embodiments, the system and method includes an application of the algorithms to use SOULS representation for machine learning systems, including generative modeling, predictive modeling, and properties optimization. That is, the SOULS can be used in AI instead of another string format or graph format. The conversions can be implemented depending on the computational protocol. Some steps may use software that uses a specific notation, and thereby the SOULS can be converted to that specific notation for those steps. In other steps, the computations may be improved by the format of the SOULS representation, and such computations can be rendered using the SOULS representation, where any other molecular representation can be converted to SOULS for such computations. For the algorithm that converts molecules into SOULS format, the data can be a set of molecular structures represented in any format, including MOL, SDF, SMI, and PDB file formats, graphs, or SMILES. For the algorithm that converts molecules in a SOULS format into any other format, the data are a set of molecules represented in SOULS format. For machine learning applications of the proposed framework, the data can be a set of molecules represented in any format. For some applications such as predictive modeling, each molecule may have an assigned set of properties.

In some embodiments, the SOULS representation can include a sequence of atomic identifiers for a molecular scaffold with decoration markers (e.g., indicators) within the sequence. The indicators identify the locations within the sequence for a chemical moiety (e.g., substituent) to be linked to the scaffold, which appear as decorations or pendants from the core scaffold of molecule. As such, the language to describe the molecules includes the scaffold to represent the core of the molecule and decorations to represent the chemical moieties (e.g., substituents) that are attached to the core molecule. The decorations can have points of attachment on the core scaffold, which points of attachment can be considered nodes, where each decoration has a node on the scaffold. The line notation can include the scaffold sequence of atomic identifiers for a scaffold with decoration markers identifying the location of the attached decoration within the sequence. The decoration markers are placed adjacent to the atom functioning as a decoration node. The decorations are then listed in a decoration sequence after the scaffold sequence, where each decoration in the decoration sequence is separated by a decoration separator (e.g., a period "."). Each decoration in the decoration sequence is adjacent with a decoration marker (e.g., *) and separated from each other with a decoration separator. As such, the SOULS representation includes a scaffold sequence and a decoration sequence. The decoration sequence includes at least one decoration. In some instances, the decoration sequence includes a plurality of decoration line notations. Each decoration has its own line notation.

The order of the decoration markers in the scaffold sequence of the scaffold define the order of the listed decorations in the decoration sequence. The typical framework includes reading from left to right, with the scaffold sequence on the left and the decoration sequence on the right; however, the orientation can be a modification thereof, such as: reading from right to left with the scaffold sequence on the right and the decoration sequence on the left; reading from right to left with the scaffold sequence on the left and the decoration sequence on the right; or from left to right with the decoration sequence on the right and the scaffold sequence on the left.

The scaffold sequence can include the atomic identifiers (e.g., atoms as represented on the periodic table) in an order with a decoration marker adjacent with the atom from which the decoration is attached. Often, the decoration marker is to the left of the decoration node atom at the initial scaffold atom, but the decoration maker may be to the right of the scaffold atom that is the decoration node atom. The decoration marker identifies the position where the decoration is present, and the order of the decoration makers identifies the order that the decorations are defined in the decoration sequence. The adjacency being left or right may be modified depending on the notation to be used. However, as presented herein the first decoration marker is to the left and is the initial character (e.g., symbol *) of the SOULS representation, and the following decoration markers are to the right of the scaffold atom that functions as the decoration node atom.

For example, a SOULS representation can read as follows:

C1Oc2ccc(*)cc2N(*)C1=O.*C.*Cl.*CC(O)CO

Here, the initial symbol is an asterisk *, which is used herein as the first decoration marker; however, it should be recognized that any other symbol (e.g., not alphanumeric) may be used. The decoration marker is then followed by the scaffold sequence C1Oc2ccc, which defines a part of the scaffold. This scaffold sequence C1Oc2ccc is then followed by the second asterisk (*), which is used as the decoration marker for the second decoration listed in the decoration sequence, where the decoration marker is to the left of the scaffold atom that functions as the decoration node. The second asterisk (*) is followed by the scaffold sequence cc2N, followed by the third asterisk (*), which is used as the decoration marker for the third decoration listed in the decoration sequence (e.g., the N is the decoration node). The third asterisk (*) is followed by the scaffold sequence C1=O, followed by a period (e.g., "."), which period indicates the end of the scaffold sequence. The subject matter following the period (e.g., decoration separator) includes the decoration sequence, which defines the decorations in the order that the asterisks are placed in the scaffold sequence. Accordingly, the first asterisk * is defined as *C, defines the first decoration in the scaffold sequence as C (e.g., carbon). The first decoration *C is followed by another period, which functions as a decoration separator. However, any symbol other than a period (e.g., not alphanumeric or used for a different designator) can be used as the decoration separator. The decoration separator period is followed by *Cl (e.g., chlorine Cl), and thereby *Cl is the second decoration that is attached to the scaffold at the location of the second decoration marker asterisk (*) in the scaffold sequence. The second decoration *C is followed by a decoration separator period and then a third decoration *CC(O)CO, which defines the chemical structure attached to the atom in the scaffold sequence having the third decoration maker (*). Therefore, this representation defines the molecular structure by parsing the structure into a scaffold and decorations, and defines the location of the decorations in an order within a line notation sequence of the molecular representation. The order of the decoration markers in the scaffold sequence defines the order that the decorations are defined in the decoration sequence. This allows for easily being able to determine the scaffold structure, the decoration structures, and then combination thereof with the decorations being attached to the scaffold as indicated by the location of the decoration markers as per the corresponding order.

As can be seen, when a decoration marker asterisk * is listed at the beginning of the scaffold sequence it is not within parentheses, but is could also be listed in parentheses if desired, so either the asterisk * or the parentheses asterisk (*) may be used as the decoration marker. Also, the decoration marker may be a vertical line, such as "|" or any other symbol. It is preferred that the decoration marker not be alpha numeric due to the need to clearly identify atoms separately from the decoration markers. The use of parentheses, or other symbology may be used in all instance of locations of decoration makers, or only within or internally of the scaffold sequence. As such, the use of parentheses around an asterisk may define that the corresponding decoration is located within the scaffold, and the lack of parentheses around the asterisk may define that the first pendent is on the first atom of the scaffold sequence.

In some embodiments, the SOULS representation includes a first character selected from a first atom identifier or a first decoration marker. In some aspects, the first character is a first atom identifier, which can be defined by the atoms of the periodic table. In some aspects, the first character can be the first decoration marker (e.g., asterisk *). The SOULS representation may include a pre-marker sequence of one or more atom identifiers before a first decoration marker. Alternatively, the SOULS representation may include a first decoration followed by a first scaffold sequence of one or more atom identifiers. The first scaffold sequence is then followed by a second decoration maker (e.g., asterisk in parentheses (*)), which identifies the preceding atom to the left of the second decoration marker as being the second scaffold node atom. The second decoration marker is followed by a second scaffold sequence and then a third decoration marker, which identifies the preceding atom to the left of the third decoration marker as being the third scaffold node atom. The third decoration marker is then followed by the final scaffold sequence, which is then followed by the first decoration separator (e.g., period "."). This first decoration separator separates the scaffold sequence from the first decoration and the entire decoration sequence. The individual decorations are separated by the decoration separator in the order they are presented as decoration markers in the scaffold sequence. Each decoration is preceded by the decoration marker (e.g., asterisk *) to identify the following characters define that decoration. Accordingly, the SOULS representation separates the scaffold structure from the decorations, which allows for improved use in various computing technologies, such as in machine learning models.

In some embodiments, a SOULS representation can include a line notation or string consists of two parts separated with a special symbol, which can be a dot or period "." as used herein, but other symbols can be defined as the decoration separator that separates the decoration sequence from the scaffold sequence. The decoration separator allows for a basic line notation of a scaffold sequence written first and a decoration sequence written afterward, or vice versa. The first part that is the scaffold sequence contains special symbols (e.g., such as asterisk '*') in positions corresponding to periphery connection points, such as the atoms of the scaffold to which the periphery decoration is connected. The second part of the SOULS representation lists the decoration sequence as individual decoration fragments (e.g., line notation of each decoration) is the same order as their corresponding connection points are listed in the scaffold sequence of the SOULS representation separated with a special symbol, for example, a dot or period '.', but may be different from the symbol separating the scaffold sequence and decoration sequence if desired. However, the dot or period can be used to denote that the following characters are the decoration line notation. Each decoration fragment is written down in a basic line notation with a connection point marked using a special symbol (such as asterisk '*'). In some aspects, the line notations in the SOULS representation are as defined and used in SMILES line notations.

FIG. 1A illustrates a method 100 of obtaining a SOULS representation. The method 100 can be implemented by obtaining a graph representation of a molecule at block 102. The graph representation is then divided into a scaffold part and at least one decoration part at block 104. Here, the decoration terminology is used to describe the chemical moieties (e.g., substituents) that are coupled to the scaffold at a decoration node atom. However, the term "decoration"

may be used interchangeably with "periphery," "pendant," or other term that identifies a chemical moiety that is attached to a scaffold. The method 100 takes the graph representation of the scaffold and identifies a first scaffold node atom that is linked to a first decoration, and presents a first decoration marker at the first scaffold node atom at block 106. The method 100 then takes the graph representation of the scaffold and converts it to a line notation (e.g., SMILES) that is ASCII compliant (e.g., each line notation is ASCII compliant), which initiates at the first scaffold node atom at block 108. Additionally, the graph representation of each decoration is converted into a corresponding line notation (e.g., SMILES or same as the scaffold line notation) at block 110. A subsequent scaffold node atom in the line notation is identified with a second decoration marker at block 112, which is repeated until all scaffold node atoms are identified with subsequent decoration markers. The decorations are arranged in a decoration sequence in the order of the decoration markers in the scaffold sequence at block 114. The SOULS representation includes the decoration sequence associated with the scaffold sequence at block 116, which can be adjacent, such as the scaffold sequence being on the left and the decoration sequence being on the right, which are separated from each other by a character that defines the separation. Thus, the SOULS representation includes the scaffold sequence having an order of decoration markers and a decoration sequence having the decorations in the order of the decoration markers.

In some embodiments, the scaffold can be identified and/or separated from the decorations by various frameworks. Different frameworks can arrive at different scaffolds. The invention allows for different scaffolds to be identified to follow the line notation for the description thereof. The invention uses the scaffold and decorations of a molecule to generate the line notation in the SOULS representation.

In some embodiments, the graph representation can be split into the scaffold and peripheral decorations using the Bemis-Murcko framework. The Bemis-Murcko framework provides for a system to separate the scaffold from the peripheral decorations by defining a scaffold as a set of ring structures and linker atoms, as well as the peripheral decorations attached to the linker atoms. A Bemis-Murcko algorithm may be used for defining the scaffold and the decorations attached thereto at nodes. This can include extracting a Bemis-Murcko scaffold from a molecular structure.

Figure 1B:
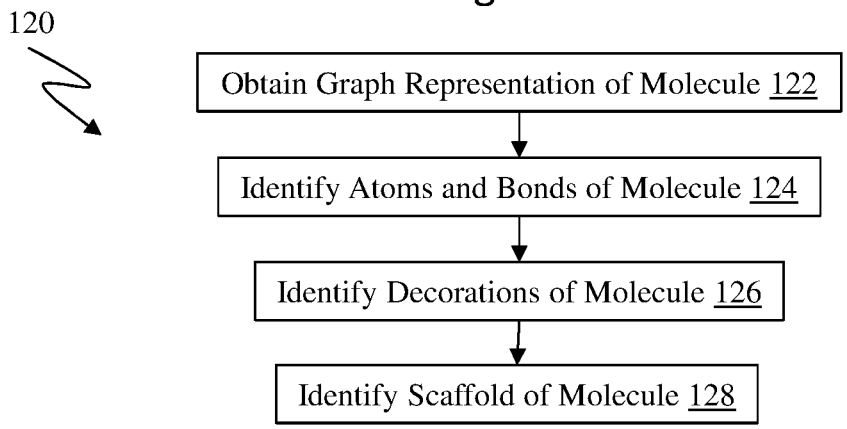
FIG. 1B provides a method for generating the scaffold and peripheral decorations from a molecule.

FIG. 1B provides a method 120 for generating the scaffold and peripheral decorations from a molecule. The method 120 can obtain the molecule as a graph representation thereof at block 122. The graph representation can then analyzed to identify nodes that are atoms and the bonds are edges at block 124. The decorations are identified and removed from decoration nodes, such that each decoration node is identified and each decoration is identified at block 126. The scaffold is identified as the remaining structure in the graph representation after the decorations are removed at block 128.

In some embodiments, the algorithm for extracting a Bemis-Murcko scaffold from a molecular structure might be as follows: (1) Represent a molecular structure as a graph, where nodes are the atoms and bonds are the edges; (2) While the molecular graph has leaf nodes, remove leaf nodes from the graph and edges connected to them; (3) The remaining graph is a Bemis-Murcko scaffold of a molecule; and (4) All nodes that were removed from the graph are a periphery of a molecule. In some aspects, the Bemis-Murcko framework might define a leaf node differently, such as nodes with at most one connected edge, or nodes with at most one connected edge corresponding to a single bond (as opposed to double or aromatic bonds). In some aspects, the decorations may be considered leaves that are attached to the leaf nodes. In any event, the protocol can parse a molecule into a scaffold and the one or more decorations attached to the decoration nodes (i.e., scaffold nodes) of the scaffold.

In some embodiments, other definitions of the scaffold instead of Bemis-Murcko are also possible and can be used in creating the SOULS representation as described herein. For example, the Bemis-Murcko framework extension in the case of periphery decorations connected to the scaffold by any bond (not only single) may be used. Also, any other algorithm that divides the molecular graph into a central part scaffold and periphery parts of decorations, where all periphery decorations are connected to each other only through the central part, can be used for scaffold-periphery definition. While the disclosure herein can refer to scaffold as Bemis-Murcko scaffold with leaf nodes defined using single bonds, it should be recognized that the scaffold and decorations can be generated with other algorithms.

Figure 2:
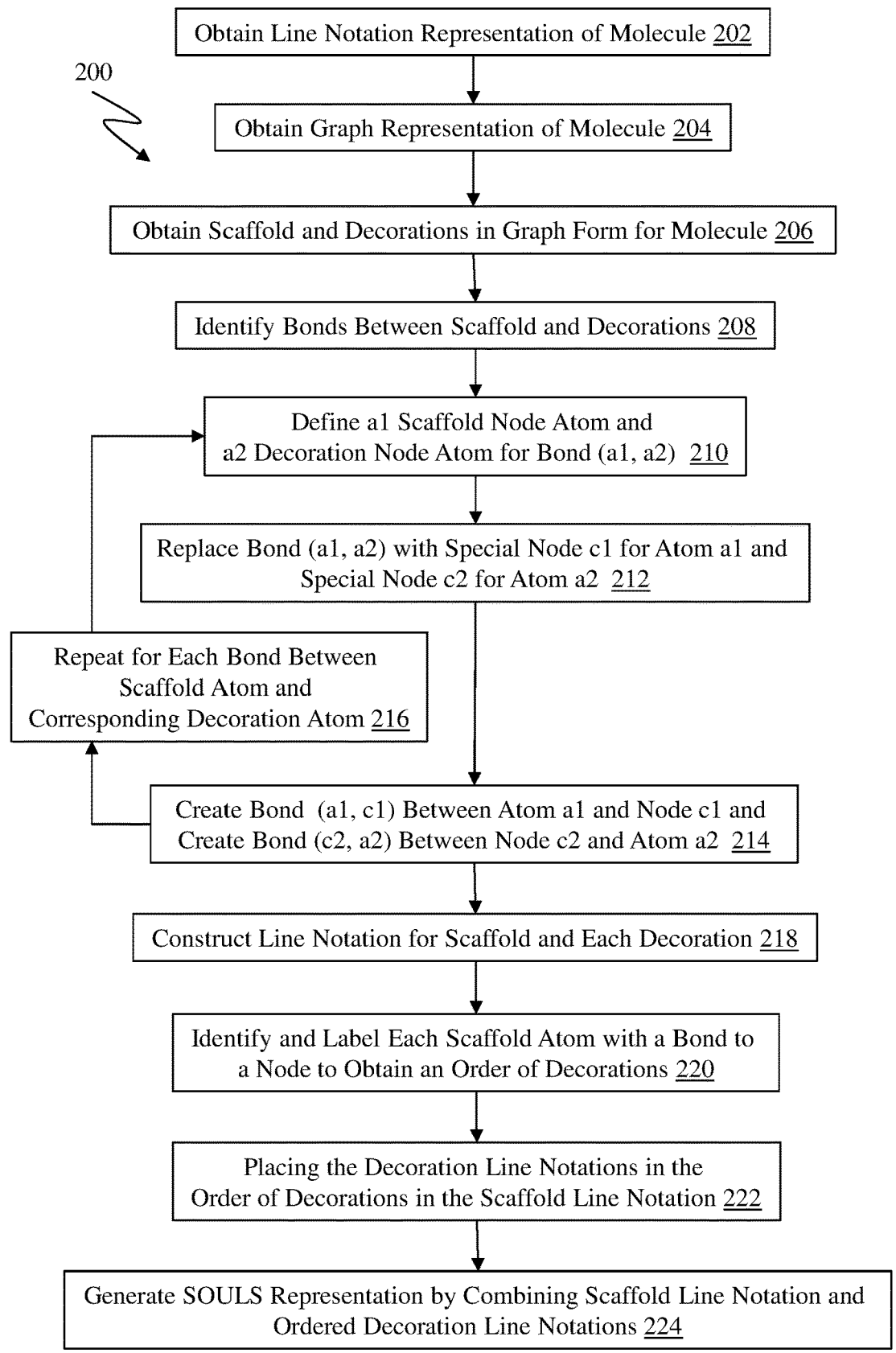
FIG. 2 illustrates a method for converting a line notation representation (e.g., SMILES representation) of a molecule into a SOULS representation of the molecule.

FIG. 2 illustrates a method 200 for converting a line notation representation (e.g., SMILES representation) of a molecule into a SOULS representation of the molecule. The method 200 includes obtaining a molecule in a line notation representation (e.g., SMILES representation) at block 202. Then, the line notation representation (e.g., SMILES representation) is converted into a graph representation of the molecule at block 204. However, it should be recognized that when available the molecule can be initially obtained in the graph representation without first starting with the line notation representation. The graph representation of the molecule is then converted into a scaffold and at least one decoration attached to the scaffold at a node at block 206. The bonds between the scaffold and decorations are then identified at block 208. The identified bonds are then labeled as bond (a1, a2), wherein a1 is the node atom in the scaffold (e.g., scaffold node atom) and a2 is the node atom in the decoration (e.g., decoration node atom), or vice versa) at block 210. The bond (a1, a2) is then removed and replaced by special node c1 (e.g., a special node) for atom a1 and by special node c2 for atom a2 at block 212. A bond (a1, c1) is then added between scaffold node atom a1 of the scaffold and special node c1 and a bond (c2, a2) is added between decoration node atom a2 of the decoration and special node c2 at block 214. The bond types of bond (a1, c1) and (c2, a2) are the same bond type as bond (a1, a2). The process of blocks 210, 212, and 214 are repeated for each bond between a scaffold atom and a corresponding decoration atom at block 216 until all of the bonds between the scaffold and decorations are removed and bonds from a scaffold node atom (e.g., a1) to a special node (e.g., c1) and a bond from a decoration node atom (e.g., a2) to a special node (e.g., c2) are generated. This separates the scaffold from the different decorations. The line notation for the scaffold and line notation for each of the decorations is constructed at block 218. The scaffold atoms with a bond to a special node (e.g., (a1, c1) are identified and labeled (e.g., with decoration marker) in the line notation for the scaffold in an order of decorations at block 220. The identification can be with a decoration marker as defined herein, such that the line notation for the scaffold includes at least one decoration marker. The order of the decoration markers in the scaffold line notation is used to order the decoration line notations at block 222.

Figure 3A:
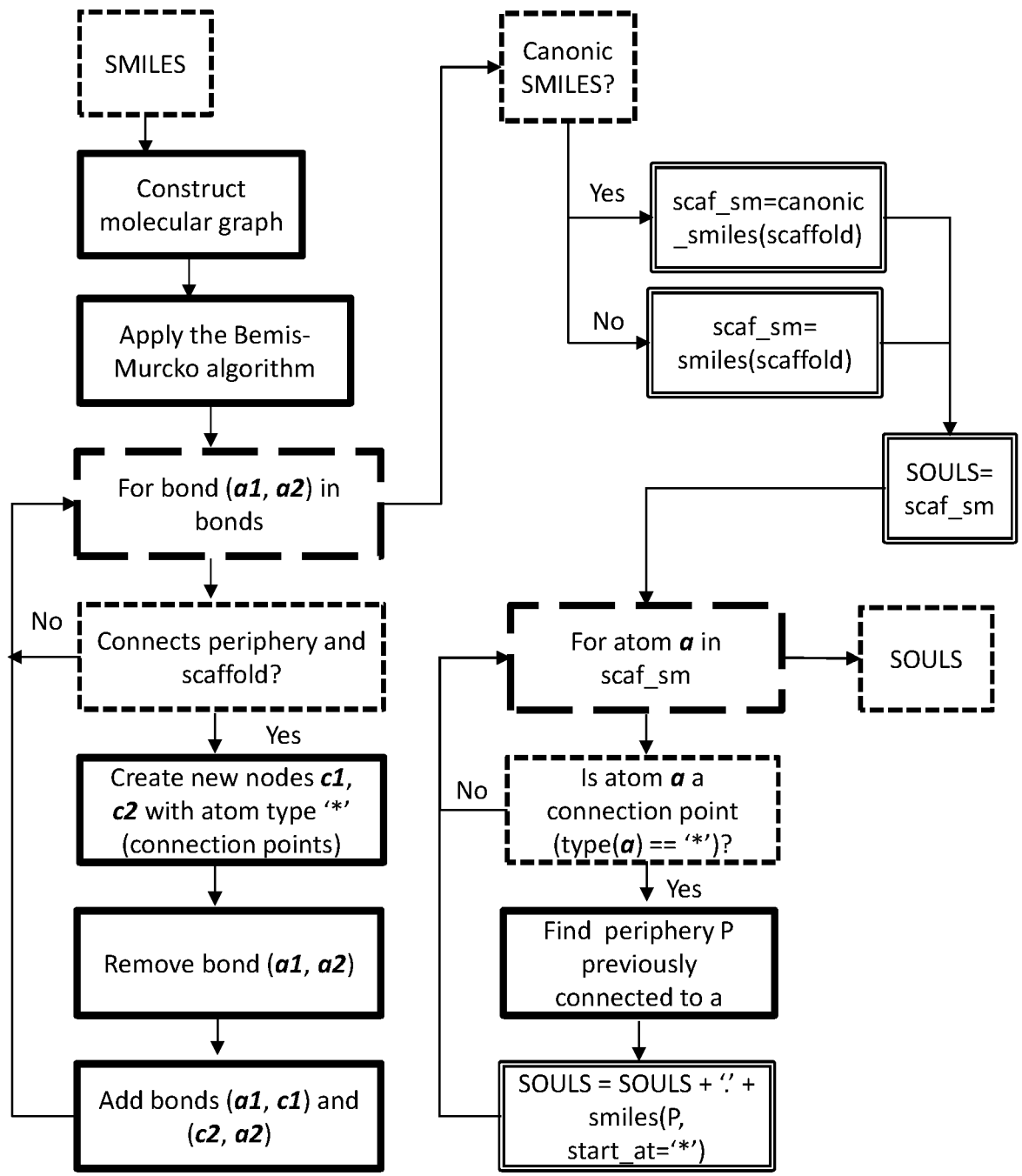
FIG. 3A provides an example of an algorithm for converting the molecular line notation SMILES into the SOULS representation, however it should be recognized that any molecular line notation can be used to generate the SOULS representation.

FIG. 3A provides an example of an algorithm for converting the molecular line notation SMILES into the SOULS representation, however it should be recognized that any molecular line notation can be used to generate the SOULS representation. Also, the algorithm may initiate when a graph representation is provided instead of a molecular line notation. The algorithm in FIG. 3A for converting SMILES into SOULS is performed as follows: (1) Construct a graph of the molecule defined in SMILES; (2) Apply the Bemis-Murcko algorithm and assign each atom to either scaffold or periphery (i.e., decoration); (3) For each bond (a1, a2) in a molecule, (3A) If ((a1 in scaffold) and (a2 in periphery)) or ((a2 in scaffold) and (a1 in periphery)); (3A1) Remove bond (a1, a2); (3A2) Create special nodes c1 and c2 with atom type '*'; (3A3) Add bonds (a1, c1) and (c2, a2) with the same bond type as (a1, a2); (3A4) repeat back to step (3A) until all bonds analyzed; (4) Construct SMILES representation of scaffold (scaf_sm=smiles(scaffold) for non-canonical SOULS representation, scaf_sm=canonic_smiles(scaffold) for canonical SOULS), wherein 'canonic_smiles is any SMILES canonicalization algorithm; (5) Start SOULS construction with constructed SMILES representation scaffold (SOULS=scaf_sm); (6) For each atom in scaf_sm, if atom_type=='*'; (6A) Find periphery P that previously was connected to this atom; (6B) Add '.' and SMILES representation of periphery starting at '*' atom to SOULS (SOULS=SOULS+'.' + smiles(P, start_at='*')); and (7) Return SOULS representation. Here, periphery P is the same as a decoration as described herein, where it is clear the chemical moiety of the structure is at the periphery thereof.

Figure 3B:
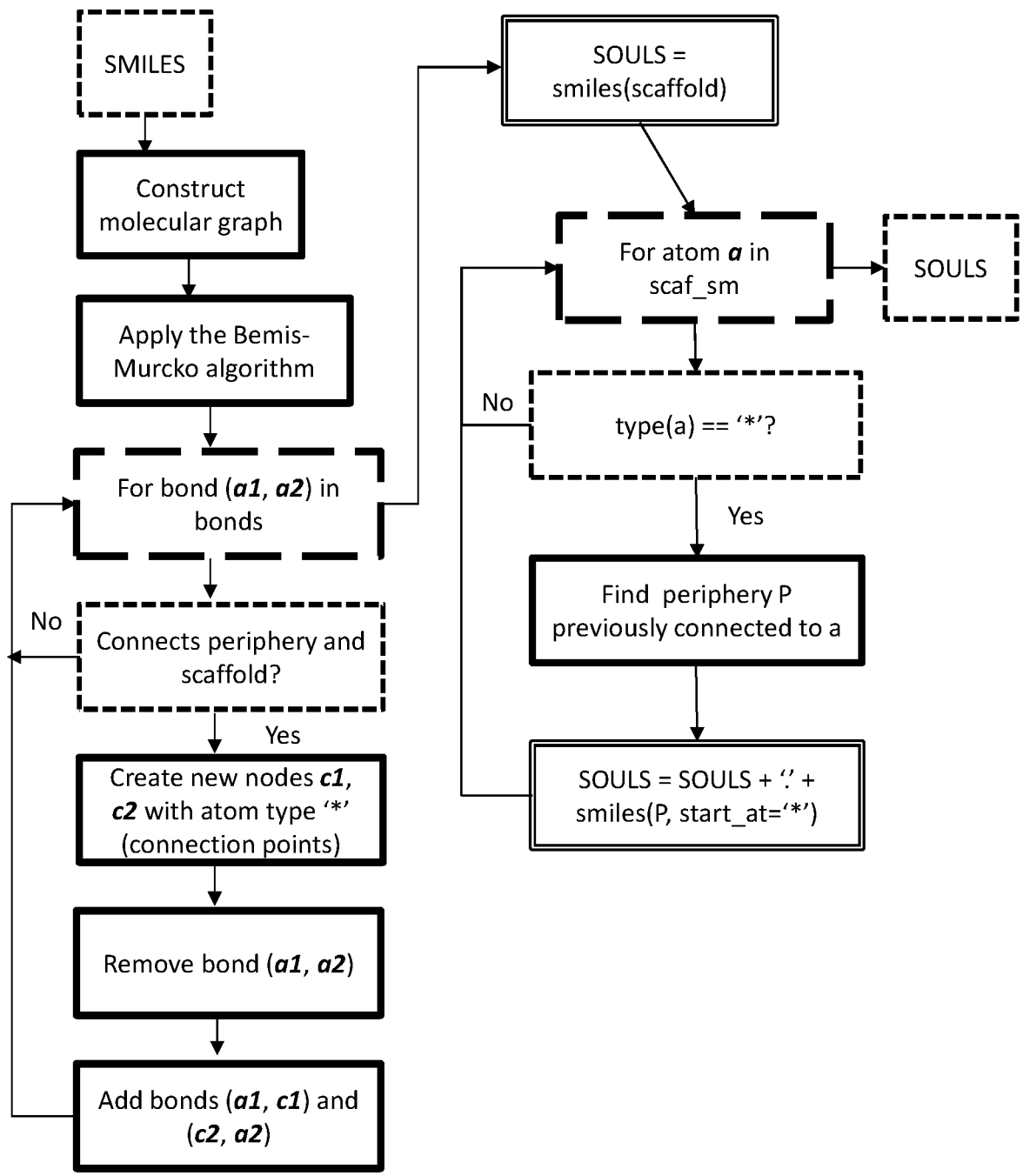
FIG. 3B shows another example of an algorithm for converting the molecular line notation SMILES into the SOULS representation, however it should be recognized that any molecular line notation can be used to generate the SOULS representation.

FIG. 3B shows another example of an algorithm for converting the molecular line notation SMILES into the SOULS representation, however it should be recognized that any molecular line notation can be used to generate the SOULS representation. Also, the algorithm may initiate when a graph representation is provided instead of a molecular line notation. The algorithm in FIG. 3B for converting SMILES into SOULS is performed as follows: (1) Construct a graph of the molecule defined in SMILES; (2) Apply the Bemis-Murcko algorithm and assign each atom to either scaffold or periphery (i.e., decoration); (3) For each bond (a1, a2) in a molecule, if ((a1 in scaffold) and (a2 in periphery)) or ((a2 in scaffold) and (a1 in periphery)); (3A) Remove bond (a1, a2); (3B) Create special node c with atom type '*'; (3C) Add bonds (a1, c) and (c, a2); (4) Start SOULS with some SMILES representation of scaffold (SOULS=smiles(scaffold)); (4) For atom in smiles (scaffold), if atom_type='*'; (4A) Find periphery P that previously was connected to this atom(4B) Add '.' and SMILES representation of periphery starting at '*' atom to SOULS (SOULS=SOULS+'.'+ smiles(P, start_at='*'); and (5) Return SOULS Representation. Here, periphery P is the same as a decoration as described herein, where it is clear the chemical moiety of the structure is at the periphery thereof.

In some embodiments, a single molecule can have multiple SOULS representations depending on the ordering of periphery decorations, or different basic line notations, or different graph traversal while constructing basic line notation. A canonical SOULS is a SOULS representation of a molecule that is obtained by applying a canonicalization algorithm to the SOULS representation. An example canonicalization algorithm when basic line notation is SMILES is given as follows: (1) Canonicalize the first part of SOULS using a SMILES canonicalization algorithm; (2) Change the order of periphery fragments in the second part of SOULS correspondingly; (3) For each periphery fragment, apply SMILES canonicalization procedure such that the connection point of the fragment will be the first symbol after canonicalization.

An example of SMILES and SOULS representations of the same molecule are given below.

Example 1

Canonical SMILES: CC1Oc2ccc(C1)cc2N(CC(O)CO)C1=O
SOULS: *C1Oc2ccc(*)cc2N(*)C1=0.*C.*Cl.*CC(O)CO
Canonical SOULS: *c1ccc2c(c1)N(*)C(=O)C(*)O2.*Cl.*CC(O)CO.*C Example 2

Canonical SMILES: CC1C2CCC(C2)C1CN(CCO)C(=O)c1ccc(C1)cc1
SOULS: C(C1C(*)C2CC1CC2)N(*)C(c1ccc(cc1)*)=O.*C.*CCO.*Cl
Canonical SOULS: *c1ccc(C(=O)N(*)CC2C3CCC(C3)C2*)cc1.*Cl.*CCO.*C Example 3

Canonical SMILES: CCCS(=O)c1ccc2[nH]c(=NC(=O)OC)[nH]c2c1
SOULS: *c1cc2c(cc1)[nH]c([nH]2)=N*.*S(=O)CCC.*C(=O)OC
Canonical SOULS: *N=c1[nH]c2ccc(*)cc2[nH]1.*C(=O)OC.*S(=O)CCC Example 4

SMILES: C #CC(C)(C)NC(=O)CN(c1cc(C)ccc1C)S(=O)(=O)c1ccccc1
Canonic SOULS: *c1ccc(*)c(N(*)S(=O)(=O)c2ccccc2)c1.*C.*C.*CC(=O)NC(C)(C)C #C
SOULS: c1cc(*)c(cc1*)N(S(=O)(=O)c1ccc-cc1)*.*C.*C.*CC(=O)NC(C)(C)C #C Example 5

The SOULS representation of Example 1 can be provided as follows:
SOULS: *C1Oc2ccc(*)cc2N(*)C1=O.*C*Cl*CC(O)CO
SOULS: *C1Oc2ccc(*)cc2N(*)C1=O.*Cl*Cl|*CC(O)CO
SOULS: *C1Oc2ccc(*)cc2N(*)C1=O.C|Cl|CC(O)CO
SOULS: *C1Oc2ccc(*)cc2N(*)C1=O.C.Cl.CC(O)CO Additionally, the SOULS representation can be used for molecule that only include a scaffold sequence and are devoid of any decorations. However, the methods of generating the SOULS representation works with molecules that are only scaffolds and lack any decorations. Accordingly, the first symbol or identifier in the SOULS representation does not have to be the decoration marker or asterisk. The leading asterisk in each decoration provided herein is not necessary, but it is useful for visualization since most SMILES visualization tools will plot such SOULS as a bunch of fragments with distinct connection points.

The SOULS representation can be checked and validated to ensure proper generation. A set of conditions for validating a SOULS is given as follows:
  Scaffold S and all periphery decoration fragments [P_1, . . . , P_n] are valid SMILES;
  Number of '*' atoms in scaffold S equals to the number of periphery decoration fragments P;
  Each periphery decoration fragments P_i contains only one '*' atom; and/or Each periphery decoration fragments P_i contains at least one non-asterisk '*' atom.

When the SOULS representation is a canonic SOULS, another rule for a valid SOULS is: Each periphery decoration fragments P_i starts with the '*' symbol.

Figure 4A:
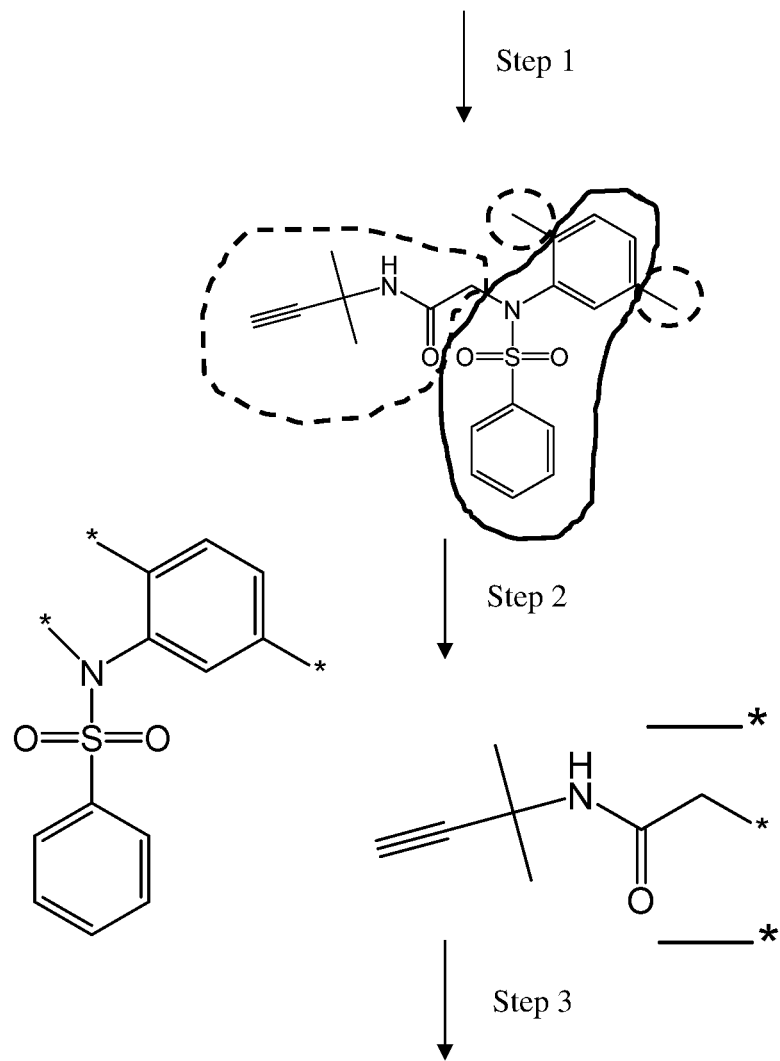
FIG. 4A shows an example of a method for converting a SMILES representation into a SOULS representation.

FIG. 4A shows an example of a method for converting a SMILES representation into a SOULS representation. Step 1 includes creating a graph representation of the molecule. Step 2 includes identifying the scaffold and periphery decorations, where the scaffold is encircled with a solid line and the periphery decorations are encircled with a dashed line. Accordingly, there is a single scaffold and three periphery decorations. Step 3 includes separating the scaffold from the periphery decorations and adding a marker (e.g., asterisk *).

Figure 4B:
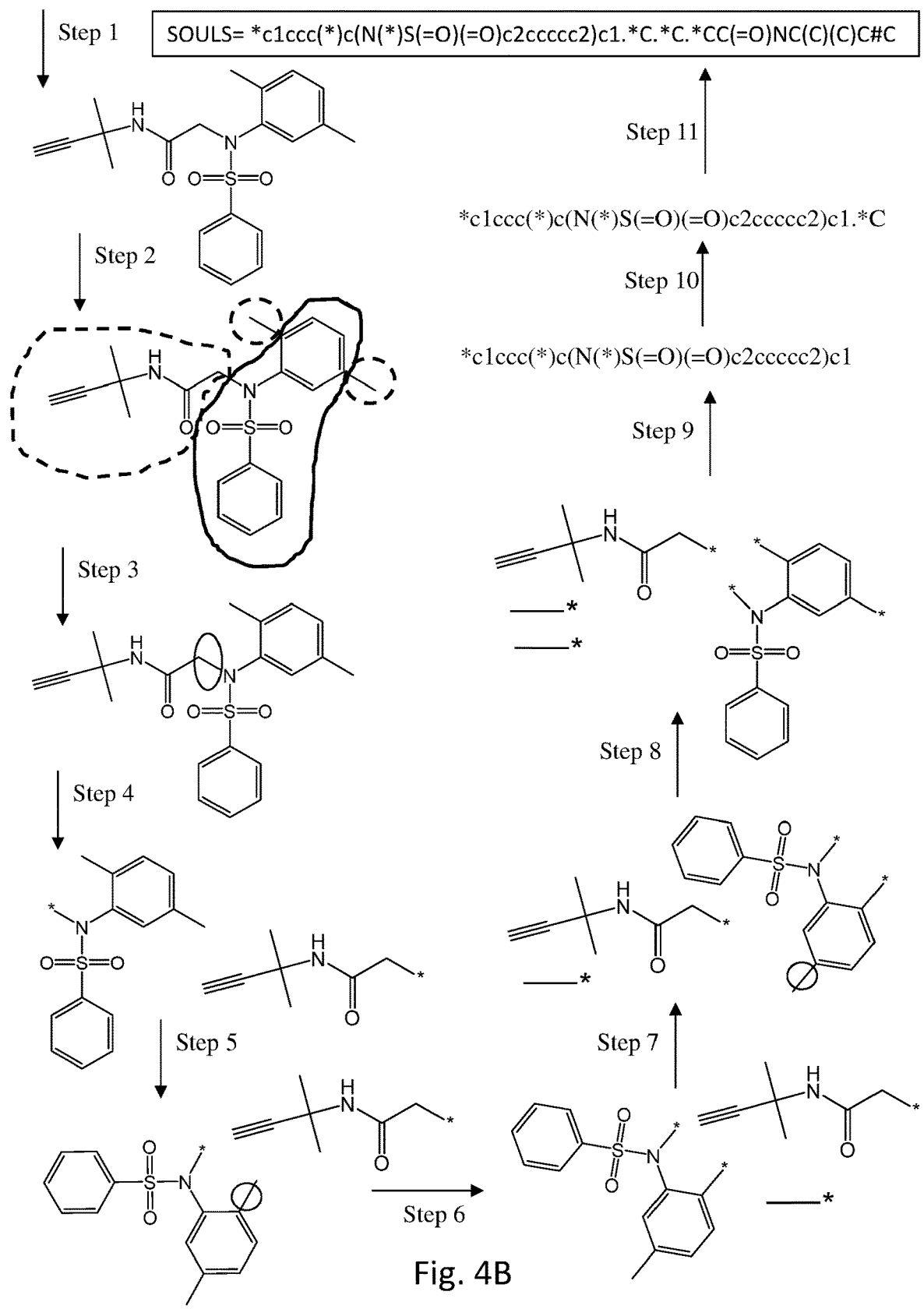
FIG. 4B shows a detailed example of a method for converting a SMILES representation into a SOULS representation.

FIG. 4B shows a detailed example of a method for converting a SMILES representation into a SOULS representation. Step 1 includes creating a graph representation of the molecule. Step 2 includes applying the Bemis Murcko algorithm to the graph representation to identify the scaffold and the periphery decorations, where the scaffold is encircled with a solid line and the periphery decorations are encircled with a dashed line. Step 3 includes iterate the molecule bond by bond until finding bond (a1, a2), as circled (e.g., between the nitrogen and carbon). Step 4 includes creating new nodes c1, c2 with atom type "*", and remove bond (a1, a2), and add bonds (a1, c1) and (c2, a2). Step 5 includes iterate the molecule bond by bond until finding bond (a1, a2), as circled (e.g., between the phenyl and methyl). Step 6 includes creating new nodes c1, c2 with atom type "*", and remove bond (a1, a2), and add bonds (a1, c1) and (c2, a2). Step 7 includes iterate the molecule bond by bond until finding bond (a1, a2), as circled (e.g., between the phenyl and other methyl). Step 8 includes creating new nodes c1, c2 with atom type "*", and remove bond (a1, a2), and add bonds (a1, c1) and (c2, a2). Step 9 includes generating line notation for scaffold (e.g., SOULS), which includes iterate atoms of scaffold until finding the attachment points of the periphery decorations. Step 10 includes adding line notation for decoration to the scaffold line notation. Step 11 includes repeating Step 9 and Step 10 for each periphery decoration until completion and providing the SOULS representation.

Additionally, the protocol for generating the SOULS representation can be reversed to generate a graph representation and/or other line notation representation, such as SMILES. The protocol can generate a graph representation that is then converted to the line notation representation. As such, the protocol can be used to convert graph representations to line notation representations.

Figure 5A:
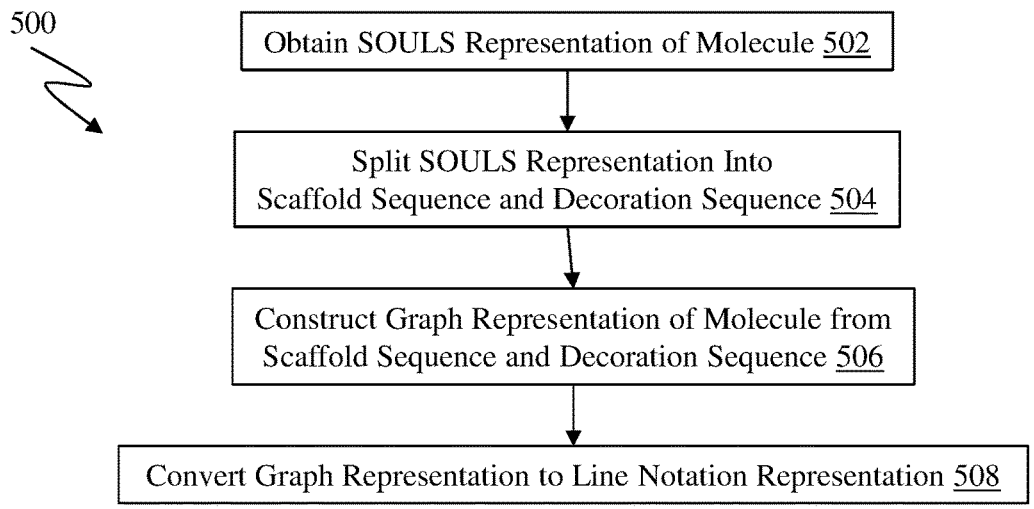
FIG. 5A shows an example of a method for converting the SOULS representation into a line notation representation, such as the SMILES representation.

FIG. 5A shows an example of a method 500 for converting the SOULS representation into a line notation representation, such as the SMILES representation. The method 500 can include obtaining a SOULS representation of a molecule at block 502. The SOULS representation is then split into a scaffold sequence line notation and a decoration sequence line notation at block 504. Here, the decoration sequence includes at least one decoration, and each decoration is defined by a line notation. As such, the decoration sequence lists all of the periphery decoration fragments. The scaffold line notation and the individual decoration line notations are then used to construct a graph representation of the molecule at step 506. The graph representation is then converted to the line notation (e.g., SMILES) representation at block 508.

Figure 5B:
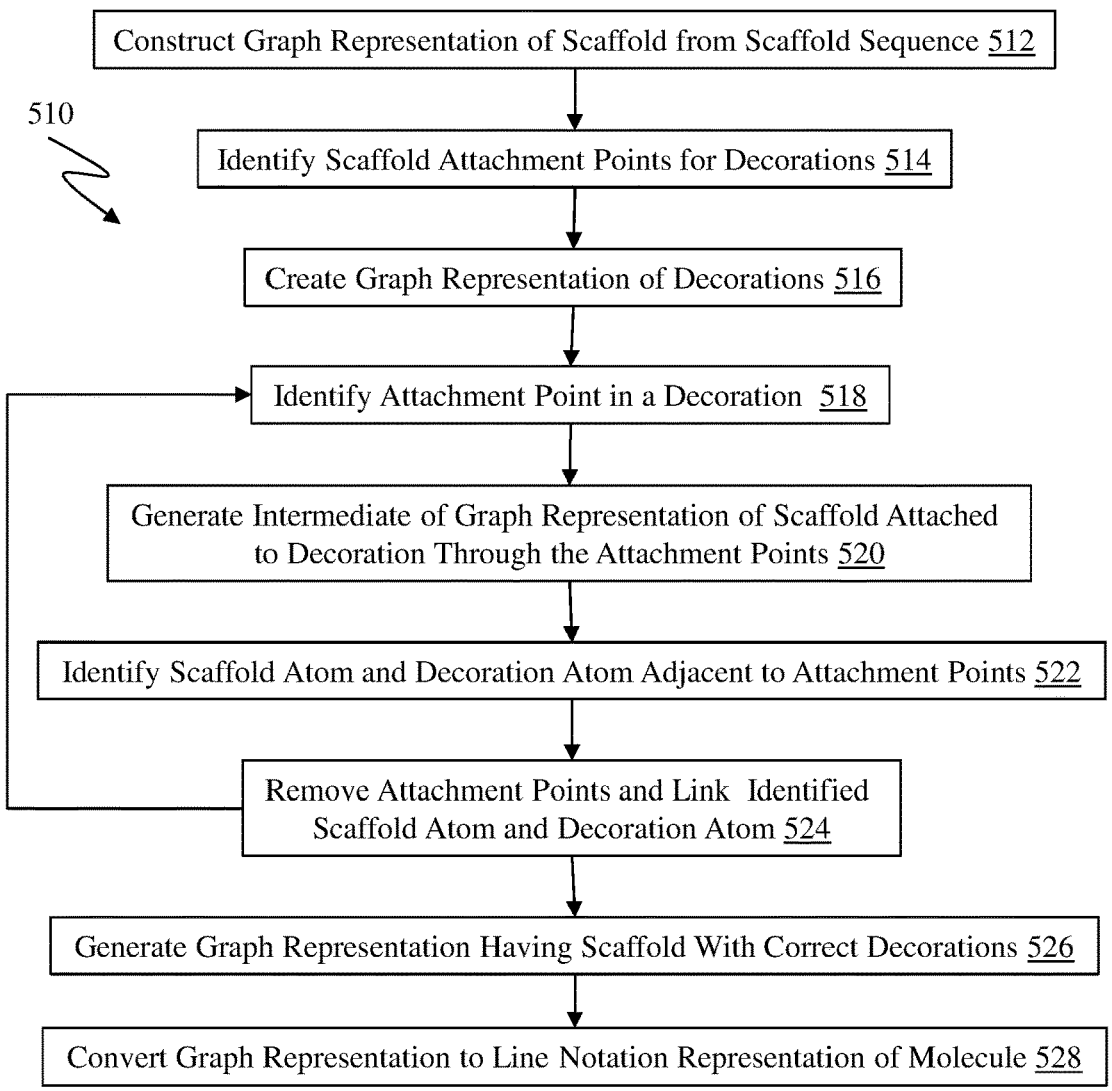
FIG. 5B shows an example method of constructing a complete graph representation of the molecule from the SOULS representation.

FIG. 5B shows an example method 510 of constructing a complete graph representation of the molecule from the SOULS representation. Here, method 510 provides additional details for block 506. The method 510 can include constructing a graph representation of the scaffold line notation at block 512. Here, the graph representation preserves the atom ordering from the scaffold sequence. Then, each atom of the graph representation is analyzed for determination of attachment points for the decorations at block 514. For an attachment point for a decoration in the scaffold, identify the correct decoration and create a graph representation of that decoration at block 516. Then, the attachment point in the graph representation of the decoration is identified at block 518. The attachment point in the scaffold graph representation and the attachment point in the decoration graph representation are linked or added together at block 520. Then, the scaffold atom and decoration atom adjacent to the attachment points are identified at block 522. The attachment points are removed and the identified adjacent scaffold atom and identified adjacent decoration atom are linked together to form the bond at block 524. The method steps from block 518 to block 524 are iterated for each atom in the scaffold that has an attachment point and for each corresponding decoration. Once the entire molecule has been iterated to attach the decorations to the scaffold, the complete graph representation of the molecule is generated at block 526. The graph representation is then converted to the line notation representation of the molecule (e.g., SMILES) at block 528. This conversion from graph representation to line representation can be performed as known or developed in the art. For example, a full SMILES representation is generated.

Figure 5C:
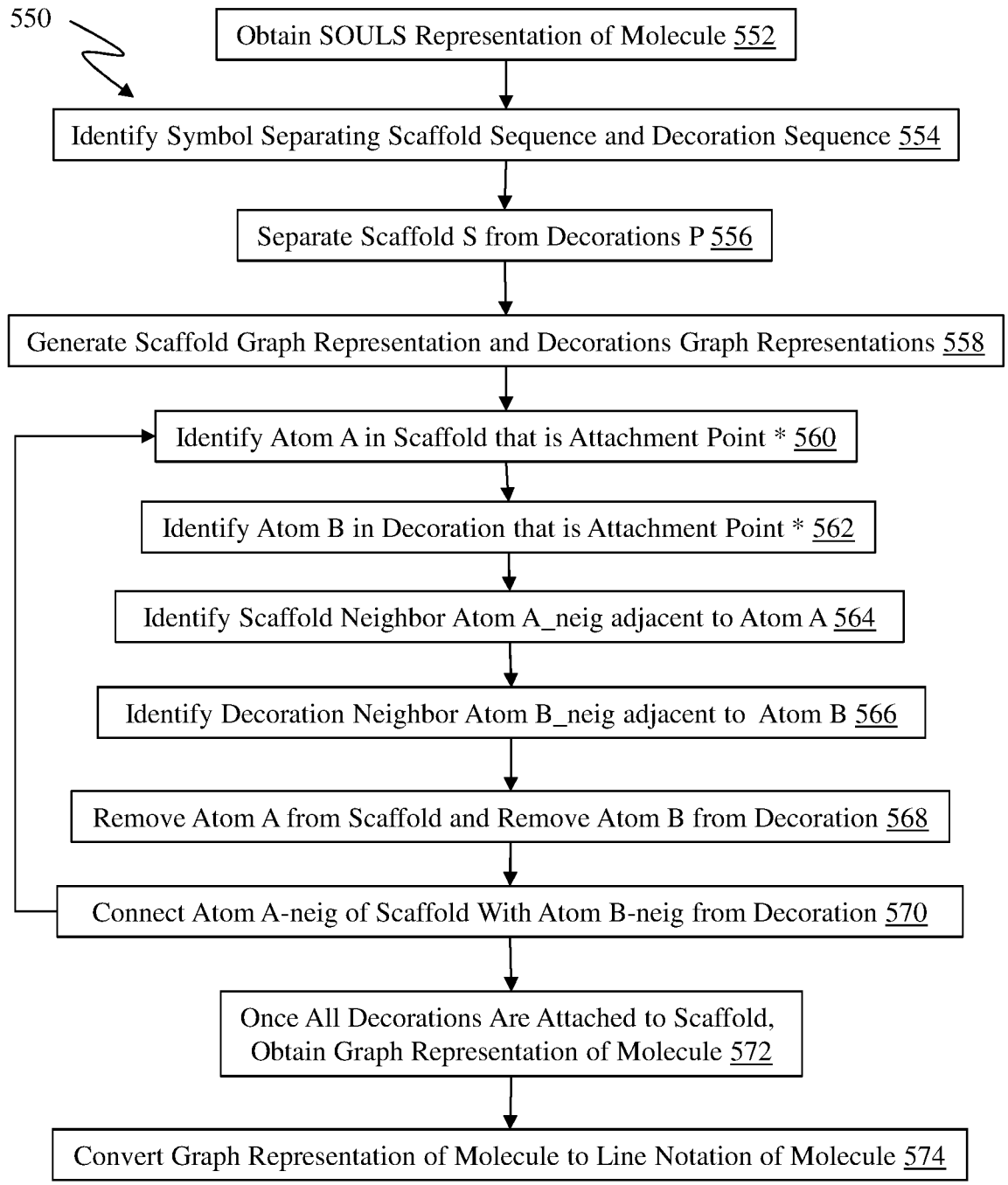
FIG. 5C shows another example method for generating SOULS or graph representation to a different line notation representation.

FIG. 5C shows another example method 550 for generating SOULS or graph representation to a different line notation representation. The method 550 can include obtaining a SOULS representation of a molecule at block 552. The symbol separating the scaffold sequence from the decoration sequence is identified at block 554, and the scaffold S is separated from the decorations P (e.g., periphery decoration) at block 556. The scaffold graph representation and decoration representations are generated at block 558. The scaffold is analyzed to identify the Atom A in the scaffold that is an attachment point * for a decoration at block 560. The atom B in the decoration that is the corresponding attachment point * is identified at block 562. The atom A_neig in the scaffold that is adjacent and a neighbor of Atom A (e.g., attachment point *) is identified at block 564. The atom B_neig in the decoration that is adjacent and a neighbor of Atom B (e.g., attachment point *) is identified at block 566. Atom A is removed from the scaffold and Atom B is removed from the decoration at block 568. The atom A_neig of the scaffold is attached to atom B_neig of the decoration (e.g., with same bond time of A-A_neig and B-B_neig) at block 570. Once all of the decorations are attached to the scaffold, the graph representation of the molecule is generated at block 572. The graph representation of the molecule is then converted to the line notation of the molecule (e.g., SMILES) at block 574.

Figure 5D:
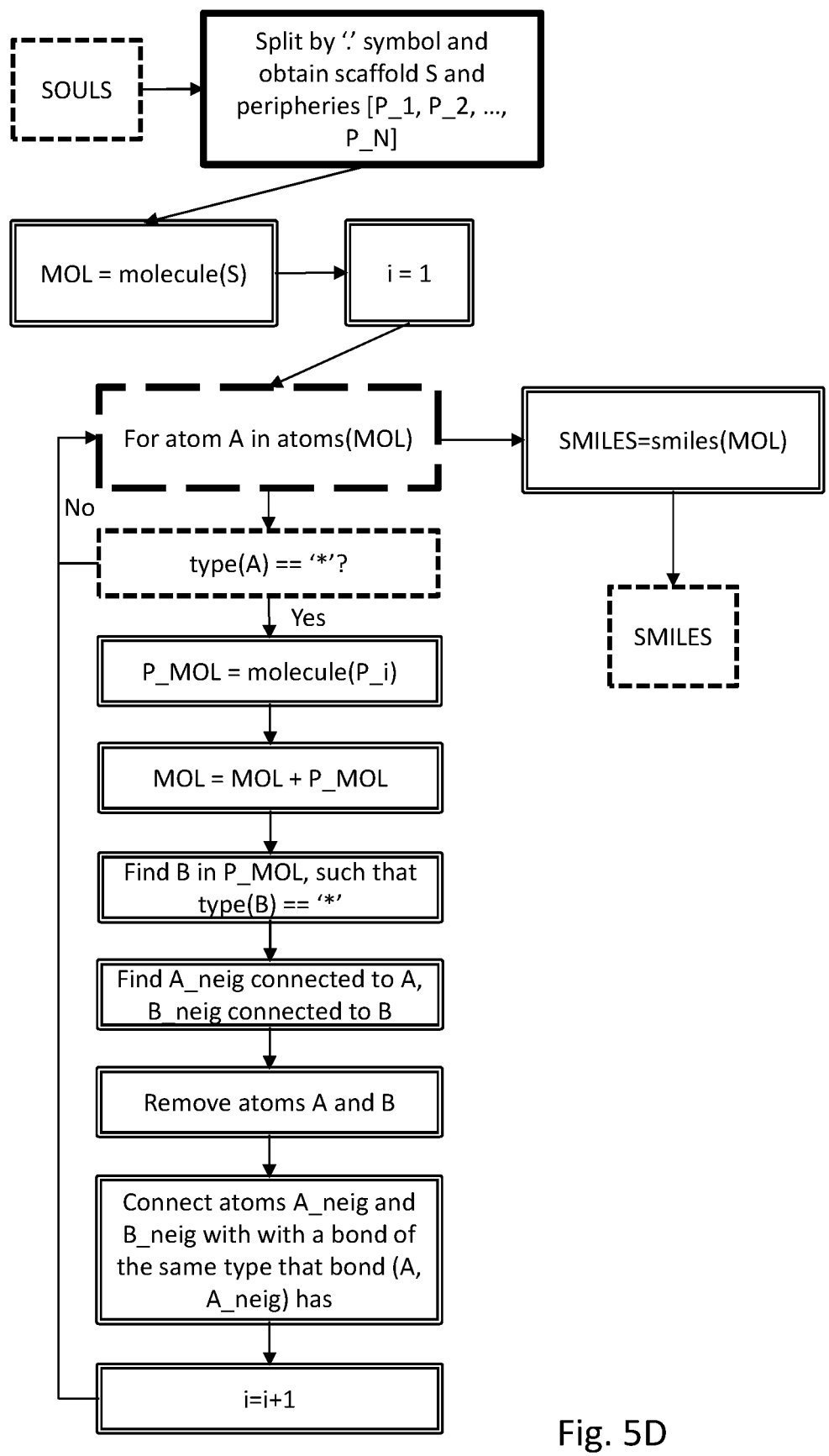
FIG. 5D provides an example of an algorithm for converting the SOULS representation into the SMILES representation, however it should be recognized that any molecular line notation can be generated from the SOULS representation.

FIG. 5D provides an example of an algorithm for converting the SOULS representation into the SMILES representation, however it should be recognized that any molecular line notation can be generated from the SOULS representation. The algorithm in FIG. 5D for converting SMILES into SOULS is performed as follows: (1) Split SOULS representation by '.' symbol and obtain scaffold S and a list of periphery fragments [P_1, P_2, P_3, ..., P_N]; (2) Construct a molecule graph MOL from scaffold S preserving atom ordering; (3) i=1; (4) For atom A in atoms of MOL (with preservation of atom ordering from S), if atom A is attachment point (atom_type(A)=='*'); (3A) Create molecule P_MOL from periphery fragment P_i; (3B) Find attachment point B in P_MOL (atom B with atom_type (B))=='*'); (3C) Add P_MOL to MOL; (3D) Define A_neig as an atom connected to attachment point A in molecule MOL; (3E) Define B_neig as an atom connected to attachment point B in fragment P_MOL; (3F) Remove attachment points A and B; (3G) Connect atoms A_neig and B_neig with a bond of the same type that bond (A, A_neig) has; (4) i=i+1 iterate until all periphery decorations attached; (5) Return SMILES representation of molecule MOL.

Figure 5E:
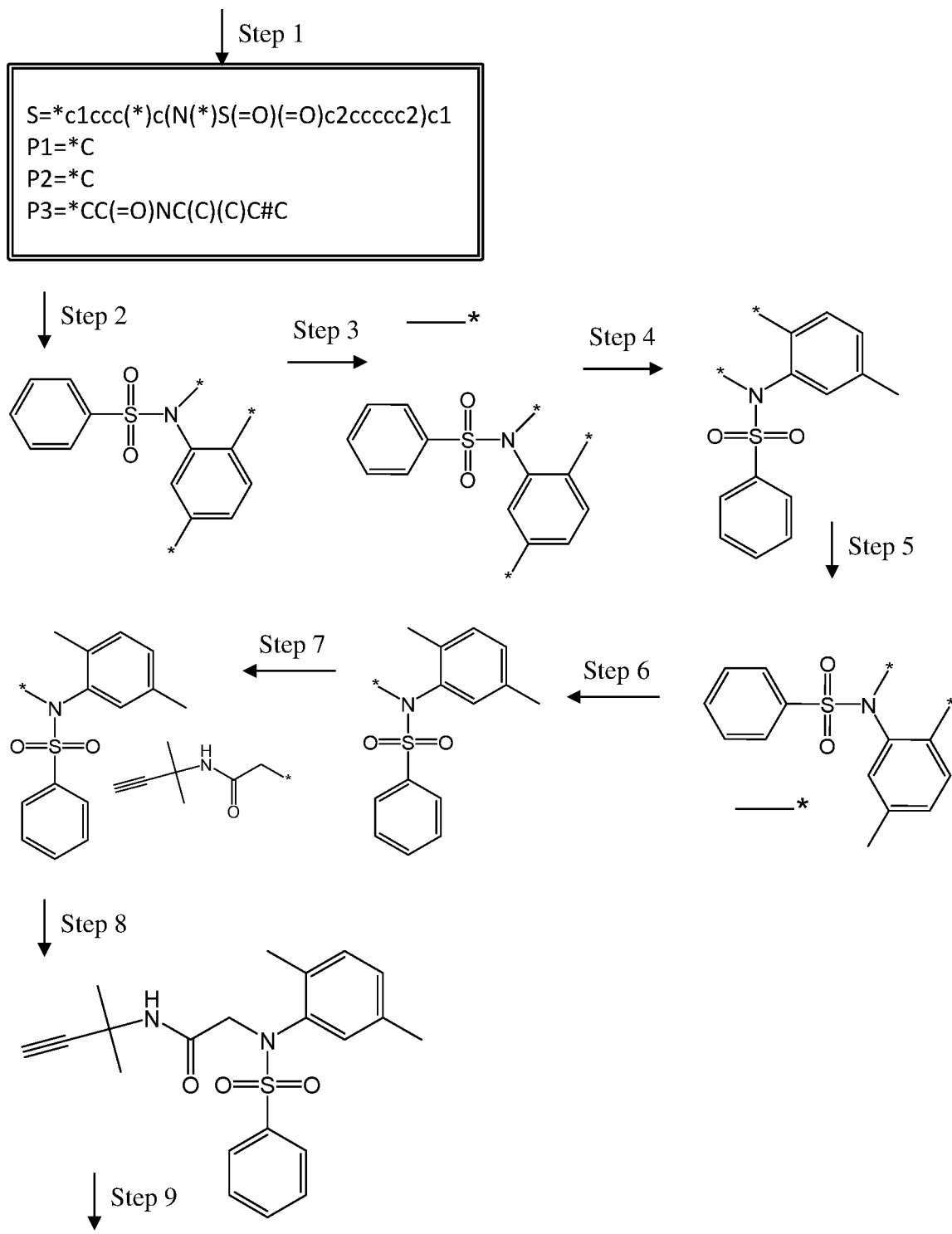
FIG. 5E shows a detailed example of a method for converting a SOULS representation into a SMILES representation.

FIG. 5E shows a detailed example of a method for converting a SOULS representation into a SOULS representation. Step 1 includes splitting the SOULS representation into the scaffold sequence S and the separate periphery decorations [P_1, P_2, ..., P_N] by identifying the at least one decoration separator, which is a period "." denoting the decoration line notation. This splits the line notation at each '.' symbol and obtains scaffold S and peripheries [P_1, P_2, ..., P_N]. Step 2 includes creating a molecular graph representation of the scaffold, and optionally each periphery decoration. Step 3 includes identifying the attachment point of the periphery decoration P1, which is a methyl. Step 4 includes attaching the periphery decoration P1 at the location defined by the corresponding decoration marker "*" on the molecule. Step 5 includes identifying the attachment point of the periphery decoration P2, which is a methyl. Step 6 includes attaching the periphery decoration P2 at the location defined by the corresponding decoration marker "*" on the molecule. Step 7 includes identifying the attachment point of the periphery decoration P3, which is a N-(2-methylbut-3-yn-2-yl)propionamide. Step 8 includes attaching the periphery decoration P3 at the location defined by the corresponding decoration marker "*" on the molecule, which completes the graph representation. Step 9 includes generating the SMILES representation from the molecular graph representation.

In some embodiments, the SOULS representation of a molecule can be used in various computing systems, such as for describing a molecule, for substantially any computing processing protocol that involves molecules. The SOULS representation is a general framework that can be applied in multiple fields, including machine learning. The machine learning protocols that can utilize the SOULS representation include supervised and unsupervised tasks in representation learning, predictive modeling, generative modeling, optimization of properties (e.g., with Bayesian optimization) or any generic algorithm involving a molecule.

In some embodiments, for predictive modeling, the SOULS representation can be used as a drop-in replacement for a SMILES representation of a molecule or any other line notation of a molecule in a computing system or in any computing protocol. The SOULS representation can be particularly useful in deep recurrent neural networks involved with computing chemical structures of molecules. Accordingly, the SOULS representation can be used for predicting different properties of molecules, including biochemical (e.g., biological pharmacokinetics or pharmacodynamics) and physical properties (e.g., solubility, vaporization temperature, or others). This allows the SOULS representation to be useful in many neural network architectures, including autoencoder-based networks for representation learning. The implantation of the SOULS representation can be as input and output for molecules represented in the SOULS representation format. The SOULS representation can also be used with other molecular representations, such as SMILES or Graphs, or converted back and forth as needed for various computational protocols. For example, an encoder-decoder model can receive the input as represented in the SOULS format, and perform the computing protocol such that there is a conversion and the output is represented in the SMILES format, or vice versa.

In some embodiments, the SOULS representation can be used in protocols for molecular properties optimization, which can include generating the representation of a molecule that satisfies the given set of properties (e.g., solubility or ease of synthesis) used in training a model or criteria for a computation. The SOULS format partitions the scaffold and separate periphery decorations for simple reading during a computation, where the ordering of the decoration markers in the scaffold sequence defining the order of the presentation of the decoration line notations provides for easier association of the scaffold and decorations. The SOULS notation is also easier to read by a human because the order of the decoration markers allows easier tracking of the defined decorations for specific attachment points. Accordingly, the SOULS representation allows for optimization by finding molecules with a high value of some quality function, which are often associated with certain scaffolds or decorations. The optimization with SOULS notation can be done with different approaches, including genetic algorithms, Bayesian optimization, and random searches as well as others.

The genetic algorithm can be exemplified as a metaheuristic inspired by the process of natural selection, which belongs to a class of evolutionary algorithms (EA). Genetic algorithms are commonly used to generate high-quality solutions to optimization and search problems by relying on biologically inspired operators such as mutation, crossover and selection. See "wikipedia.org/wiki/Genetic_algorithm," which is incorporated herein by specific reference. The SOULS representation can be used for defining a chemical structure when used in any genetic algorithm.

Also, the SOULS representation can be used for creating analogs of chemical structures. The SOULS notation can be used to swap different decorations for a specific scaffold, or to swap scaffolds for different but similar structures that can have the same number and placement of the decorations. For example, for generation of analogs, a possible mutation procedure is replacing random periphery fragments with random periphery fragments from other molecules. As such, the improved SOULS notation allows for easy substituent substitution on a scaffold by switching or swapping one decoration line notation for the line notation of another, which significantly simplifies the process The SOULS notation is configured for easy mutation and modification of peripheral decorations, such that a library of substituents can be provided to the molecule at specific locations by identifying the order of the decoration marker in the scaffold sequence and then tracking the ordered decoration line notations in the decoration sequence. Similarly, the SOULS notation allows for the scaffold sequence to be modified or replaced with a different scaffold sequence so that the computer can process mutations by replacing the scaffold of a molecule with a scaffold from another different molecule with the same number of periphery fragments. Thus, the SOULS notation can be used for creating analogs of chemical scaffolds as well as analogs that have the same or related chemical scaffold with an array of different substituent patterns.

A scaffold-oriented line notation for a chemical structure includes: a scaffold sequence of atom identifiers arranged in a line notation defining a scaffold of a chemical structure, the scaffold sequence includes at least one decoration marker; a decoration separator following a last atom identifier or a last decoration marker of the scaffold sequence; at least one decoration having at least one atom identifier of a line notation defining a chemical structure of a decoration attached to the scaffold; in the scaffold sequence, an order of the decoration markers defines an order of the decorations; in the scaffold sequence, the first atom identifier is adjacent to a first decoration marker; in the at least one decoration, the first decoration follows the first decoration separator; in the at least one decoration, the first decoration is attached to the first atom identifier.

In some embodiments, a scaffold-oriented line notation for a chemical structure can include: a scaffold sequence of a plurality of atom identifiers arranged in a line notation that defines a scaffold of a chemical structure of a molecule, wherein the scaffold sequence includes at least one decoration marker located at one of: preceding a first atom identifier of the scaffold sequence; preceding a subsequent/second atom identifier; or following the subsequent/second atom identifier; a decoration separator following a last atom identifier or a last decoration marker of the scaffold sequence; at least one decoration having at least one atom identifier of a line notation that defines a chemical structure of a periphery decoration that is attached to the scaffold of the molecule; wherein: in the scaffold sequence, an order of the at least one decoration marker defines an order of the at least one decoration; in the scaffold sequence, the first atom identifier is adjacent to a first decoration marker; in the at least one decoration, the first decoration follows the first decoration separator; in the at least one decoration, the first decoration is defined as being attached to the first atom identifier in a chemical structure of the molecule. In some aspects, the first decoration marker precedes the first linker atom identifier of the scaffold sequence. The first linking atom can be any atom including the first atom or last atom or any atom therebetween in the scaffold sequence.

In some embodiments, the scaffold-oriented line notation includes: at least a second decoration marker adjacent with the second atom identifier; at least a second decoration separator following the first decoration; and at least a second decoration following the at least one second decoration separator, wherein each second decoration is separated by a second decoration marker.

In some embodiments, the scaffold-oriented line notation includes: a plurality of decoration markers adjacent with the corresponding atom identifier; a plurality of decoration separators separated by a plurality of decorations; and each of the plurality of decorations following a corresponding decoration separator.

In some embodiments, each decoration includes a corresponding decoration marker followed by a line notation of the chemical structure of the decoration.

In some embodiments, each atom identifier is defined by the periodic table. In some aspects, each decoration marker is a symbol. In some aspects, each decoration separator is a second symbol different from the decoration maker symbol. In some aspects, each decoration marker in the scaffold sequence is bound by a third symbol that is different from the decoration maker symbol and the decoration separator symbol.

In some embodiments, a method of converting a line notation of a chemical structure to the scaffold-oriented line notation for the chemical structure of one of the embodiments can include: providing the line notation of the chemical structure; converting the line notation to a graph notation of the chemical structure; identifying a scaffold and at least one decoration of the graph notation of the chemical structure; separating the scaffold from the at least one decoration; converting a graph representation of the scaffold to a corresponding line notation representation of the scaffold; converting a graph representation of each decoration to a corresponding line notation representation of each decoration; identify a first linking atom in the scaffold attached to a first decoration; placing a first decoration marker adjacent to the first linking atom; placing a first decoration separator following the last atom identifier or the last decoration marker of the scaffold sequence; placing a first decoration following the first decoration separator; and providing the scaffold-oriented line notation for the chemical structure. The first linking atom can be any atom including the first atom or last atom or any atom therebetween in the scaffold sequence.

In some embodiments, the method includes: identifying each atom and each bond of the chemical structure of the molecule; identifying the scaffold of the chemical structure; identifying each decoration that is attached to an atom of the scaffold; identifying each bond between each decoration and corresponding atom of the scaffold; and breaking the identified bond between each decoration and corresponding atom of the scaffold.

In some embodiments, the method includes: replacing each broken bond with a scaffold node linked to the corresponding atom of the scaffold; and replacing each broken bond with a decoration node lined to each decoration.

In some embodiments, the method includes: constructing a line notation of the scaffold having a decoration marker for each scaffold node; and constructing a line notation of each decoration.

In some embodiments, the method includes: determining an order of the at least one decoration marker in the line notation of the scaffold; and arranging the at least one decoration in a decoration sequence having the order of the at least one decoration marker in the line notation of the scaffold, wherein each decoration has the decoration line notation and is separated by a decoration separator.

In some embodiments, the method includes: arranging the scaffold sequence so that the first decoration marker precedes the first linking atom identifier of the scaffold sequence. The first linking atom can be any atom including the first atom or last atom or any atom therebetween in the scaffold sequence.

In some embodiments, the method includes arranging the line notation to include: at least a second decoration marker adjacent with the second linking atom identifier; at least a second decoration separator following the first decoration; and at least a second decoration following the at least one second decoration separator, wherein each second decoration is separated by a second decoration marker.

In some embodiments, the method includes arranging the line notation to include: a plurality of decoration markers adjacent with the corresponding linking atom identifier; a plurality of decoration separators separated by a plurality of decorations; and each of the plurality of decorations following a corresponding decoration separator.

In some embodiments, the method includes defining each decoration to include a corresponding decoration marker followed by a line notation of the chemical structure of the decoration.

In some embodiments, the method includes at least one of: each atom identifier is defined by the periodic table; each decoration marker is a symbol; each decoration separator is a second symbol different from the decoration maker symbol; or each decoration marker in the scaffold sequence is bound by a third symbol that is different from the decoration maker symbol and the decoration separator symbol.

In some embodiments, a method of converting the scaffold-oriented line notation (e.g., SOULS) for the chemical structure to a different line notation (e.g., SMILES) of the chemical structure can include: providing the scaffold-oriented line notation for the chemical structure; splitting the scaffold-oriented line notation into the scaffold sequence and each decoration; constructing a graph representation of the scaffold sequence; constructing a graph representation of each decoration; combining the graph representation of the scaffold sequence and graph representation of each decoration to form a graph representation of the molecule; and converting the graph representation of the molecule to the different line notation.

In some embodiments, the method (e.g., SOULS to SMILES) includes: identifying a scaffold attachment point on the graph representation of the scaffold for each decoration; identifying the scaffold atom attached to scaffold attachment point for each decoration; and removing each scaffold attachment point.

In some embodiments, the method (e.g., SOULS to SMILES) includes: identifying a decoration attachment point on the graph representation of each decoration; identifying a decoration atom attached to the decoration attachment point for each decoration; and removing each decoration attachment point.

In some embodiments, the method (e.g., SOULS to SMILES) includes: connecting each scaffold atom with the corresponding decoration atom with a bond; and providing the graph representation of the chemical structure of the molecule.

In some embodiments, the method (e.g., SOULS to SMILES) includes identifying a first decoration separator and each decoration separator between each decoration, the first decoration separator following the last atom identifier or last decoration marker;

In some embodiments, the method (e.g., SOULS to SMILES) includes identifying atom A in the scaffold defining an attachment point to a decoration; identifying atom B in a decoration defining an attachment point to the scaffold; identifying atom A_neig bonded to atom A; identifying atom B_neig bonded to atom B; removing atom A; removing atom B; and connecting atom A_neig by a bond to atom B_neig.

In some embodiments, the method (e.g., SOULS to SMILES) includes: identifying each atom A in the scaffold defining an attachment point to a decoration; identifying each atom B in each decoration defining an attachment point to the scaffold; identifying each atom A_neig bonded to each atom A; identifying each atom B_neig bonded to atom each B; removing each atom A; removing each atom B; and connecting each atom A_neig by a bond to each corresponding atom B_neig.

In some embodiments, a method of computing a chemical structure can include: providing the scaffold-oriented line notation for the chemical structure of one of the embodiments into a computing system; and performing a computation protocol with the scaffold-oriented line notation with the computing system.

In some embodiments, a computer program product can include: a non-transient, tangible memory device having computer-executable instructions that when executed by a processor, cause performance of the method of converting a line notation of a chemical structure to the scaffold-oriented line notation for the chemical structure of one of the embodiments.

In some embodiments, a computer program product can include: a non-transient, tangible memory device having computer-executable instructions that when executed by a processor, cause performance of the method of converting the scaffold-oriented line notation for the chemical structure to a different line notation of the chemical structure.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In one embodiment, the present methods can include aspects performed on a computing system. As such, the computing system can include a memory device that has the computer-executable instructions for performing the method. The computer-executable instructions can be part of a computer program product that includes one or more algorithms for performing any of the methods of any of the claims.

In one embodiment, any of the operations, processes, methods, or steps described herein can be implemented as computer-readable instructions stored on a computer-readable medium. The computer-readable instructions can be executed by a processor of a wide range of computing systems from desktop computing systems, portable computing systems, tablet computing systems, hand-held computing systems as well as network elements, base stations, femtocells, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Figure 6:
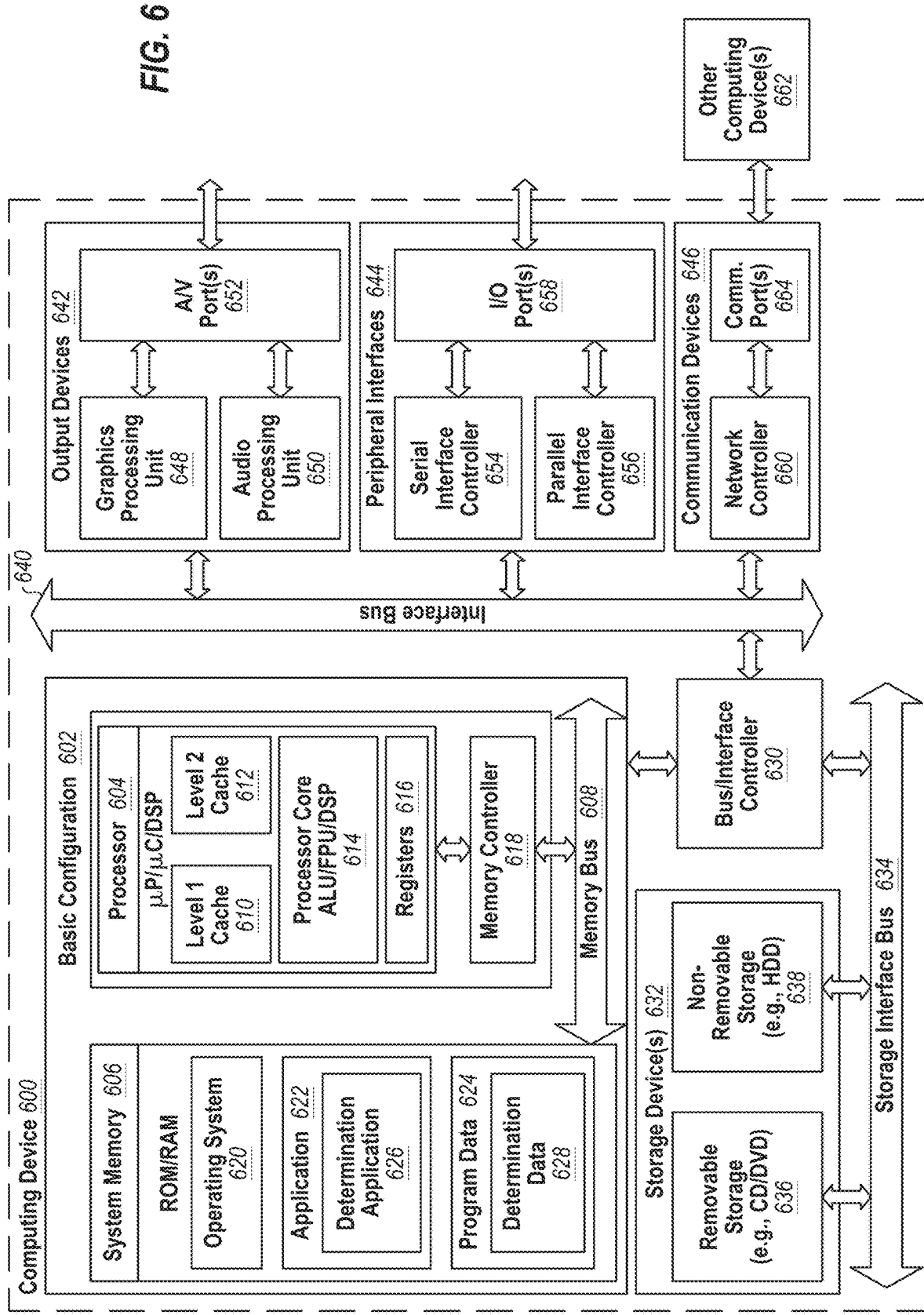
FIG. 6 shows an example of a computer or computing system configured for performing the computations and methods described herein.

FIG. 6 shows an example computing device 600 that is arranged to perform any of the computing methods described herein. In a very basic configuration 602, computing device 600 generally includes one or more processors 604 and a system memory 606. A memory bus 608 may be used for communicating between processor 604 and system memory 606.

Depending on the desired configuration, processor 604 may be of any type including but not limited to a microprocessor (uP), a microcontroller (uC), a digital signal processor (DSP), or any combination thereof. Processor 604 may include one more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations memory controller 618 may be an internal part of processor 604.

Depending on the desired configuration, system memory 606 may be of any type including but not limited to volatile memory (such as RAM), non-volatile memory (such as ROM, flash memory, etc.) or any combination thereof. System memory 606 may include an operating system 620, one or more applications 622, and program data 624. Application 622 may include a determination application 626 that is arranged to perform the functions as described herein including those described with respect to methods described herein. Program Data 624 may include determination information 628 that may be useful for analyzing the contamination characteristics provided by the sensor unit 240. In some embodiments, application 622 may be arranged to operate with program data 624 on operating system 620 such that the work performed by untrusted computing nodes can be verified as described herein. This described basic configuration 602 is illustrated in FIG. 6 by those components within the inner dashed line.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module" or "component" can refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modulates running on a computing system.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an"

limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

This patent application cross-references: U.S. application Ser. No. 16/015,990 filed Jun. 2, 2018; U.S. application Ser. No. 16/134,624 filed Sep. 18, 2018; U.S. application Ser. No. 16/562,373 filed Sep. 5, 2019; U.S. Application No. 62/727,926 filed Sep. 6, 2018; U.S. Application No. 62/746,771 filed Oct. 17, 2018; and U.S. Application No. 62/809,413 filed Feb. 22, 2019; which applications are incorporated herein by specific reference in their entirety. All references recited herein are incorporated herein by specific reference in their entirety.

The invention claimed is:

1. One or more non-transitory computer-readable media storing instructions that, when executed by one or more processors, cause a system to perform operations, the operations comprising:
   obtaining a chemical structure with a computing system; and
   converting the chemical structure to a computer-readable scaffold-oriented line notation, the scaffold-oriented line notation comprising:
      a scaffold sequence of a plurality of atom identifiers arranged in a line notation that defines a scaffold of the chemical structure of a molecule, wherein the scaffold sequence includes at least one decoration marker, each decoration marker being adjacent to an atom identifier of a linking atom of the scaffold that is linked to a decoration, wherein in the chemical structure of the molecule the decoration is a chemical moiety that is bonded to the linking atom of the scaffold;
      a decoration separator following a last atom identifier or a last decoration marker of the scaffold sequence;
      at least one decoration having at least one atom identifier in a line notation that defines a chemical structure of the chemical moiety of the decoration that is attached to the linking atom of the scaffold of the molecule;
   wherein:
      in the scaffold sequence, an order of the at least one decoration marker defines an order of the at least one decoration;
      in the at least one decoration, the first decoration follows the first decoration separator; and
      in the at least one decoration, the first decoration is defined as being attached to a first linking atom identifier in the plurality of atom identifiers between a first atom identifier and the last atom identifier, wherein the first linking atom is any atom including a first atom or last atom or any atom therebetween in the scaffold sequence.

2. The non-transitory computer-readable media of claim 1, wherein the at least one decoration marker is located at one of: preceding a first atom identifier of the scaffold sequence that is bonded to a first decoration; following the first atom identifier of the scaffold sequence that is bonded to the first decoration; preceding a first linking atom identifier of the scaffold sequence that is bonded to a first decoration, wherein the first linking atom identifier is not the first atom identifier in the scaffold sequence; following the first linking atom identifier of the scaffold sequence that is bonded to the first decoration; preceding a subsequent atom identifier of the scaffold sequence that is bonded to the first decoration; or following the subsequent atom identifier of the scaffold sequence that is bonded to the first decoration.

3. The non-transitory computer-readable media of claim 2, comprising:
at least a subsequent decoration marker adjacent with the subsequent atom identifier;
at least a subsequent decoration separator following the first decoration; and
at least a subsequent decoration following the at least one subsequent decoration separator, wherein each subsequent decoration is separated by a subsequent decoration marker.

4. The non-transitory computer-readable media of claim 1, wherein in the scaffold sequence, a first linking atom identifier of the plurality of atom identifiers is adjacent to a first decoration marker.

5. The non-transitory computer-readable media of claim 1, comprising a first decoration marker preceding the first atom identifier of the scaffold sequence.

6. The non-transitory computer-readable media of claim 1, comprising:
a plurality of decoration markers adjacent with the corresponding atom identifier;
a plurality of decorations separated by a plurality of decoration separators; and
each of the plurality of decorations following a corresponding decoration separator.

7. The non-transitory computer-readable media of claim 1, comprising each decoration including a corresponding decoration marker followed by a line notation of the chemical structure of the decoration.

8. The non-transitory computer-readable media of claim 1, wherein each atom identifier is defined by the periodic table.

9. The non-transitory computer-readable media of claim 8, wherein each decoration marker is a symbol.

10. The non-transitory computer-readable media of claim 9, wherein each decoration separator is a second symbol different from the decoration maker symbol.

11. The non-transitory computer-readable media of claim 10, wherein each decoration marker in the scaffold sequence is bound by a third symbol that is different from the decoration maker symbol and the decoration separator symbol.

12. The non-transitory computer-readable media of claim 1, the operations comprising converting a line notation of a chemical structure of a molecule to the scaffold-oriented line notation for the chemical structure by:
obtaining, by a computer, the line notation of the chemical structure;
converting, by the computer, the line notation to a graph notation of the chemical structure;
identifying a scaffold of the graph notation of the chemical structure;
for identifying any decoration attached to the scaffold of the graph notation of the chemical structure;
separating the identified scaffold from any decoration;
converting, by the computer, a graph representation of the scaffold to a corresponding line notation representation of the scaffold, wherein the line notation includes a plurality of atom identifiers arranged in a scaffold sequence;
converting a graph representation of any decoration to a corresponding line notation representation of each decoration;
identifying a first linking atom in the scaffold attached to a first decoration, when a first decoration is present and linked to the first linking atom in the chemical structure;
identifying a first linking atom identifier of the first linking atom in the scaffold sequence when the first linking atom is identified;
placing a first decoration marker adjacent to the first linking atom identifier in the scaffold sequence, when the first decoration is present in the chemical structure;
placing a first decoration separator following the last atom identifier or the last decoration marker of the scaffold sequence;
placing the first decoration following the first decoration separator, when the first decoration is present in the chemical structure;
providing, by the computer, a scaffold-oriented line notation for the chemical structure; and
performing, by the computer, a computation protocol with the scaffold-oriented line notation.

13. The computer-readable media of claim 12, the operations further comprising:
identifying at least one decoration of the graph notation of the chemical structure;
separating the scaffold from the at least one decoration;
converting a graph representation of each decoration to a corresponding line notation representation of each decoration;
identify the first linking atom identifier in the scaffold sequence for the first linking atom attached to the first decoration of the identified at last one decoration;
placing the first decoration marker adjacent to the first linking atom identifier;
placing the first decoration following the first decoration separator; and
providing the scaffold-oriented line notation for the chemical structure, wherein the scaffold-oriented line notation includes the scaffold sequence and a decoration sequence of the at least one decoration, wherein the scaffold sequence and decoration sequence are separated by the first decoration separator.

14. The computer-readable media of claim 13, wherein the scaffold-oriented line notation includes:
the scaffold sequence of the plurality of atom identifiers arranged in the line notation that defines the scaffold of the chemical structure of the molecule, wherein the scaffold sequence includes the at least one decoration marker, each decoration marker being adjacent to the atom identifier of the linking atom of the scaffold that is linked to the decoration, wherein in the chemical structure of the molecule the decoration is the chemical moiety that is bonded to the linking atom of the scaffold;
the decoration separator following the last atom identifier or the last decoration marker of the scaffold sequence;
the at least one decoration having at least one atom identifier in a line notation that defines the chemical structure of the chemical moiety of the decoration that is attached to the linking atom of the scaffold of the molecule;
wherein:
in the scaffold sequence, an order of the at least one decoration marker defines an order of the at least one decoration;
in the at least one decoration, the first decoration follows the first decoration separator; and
in the at least one decoration, the first decoration is defined as being attached to the first linking atom identifier in the plurality of atom identifiers between a first atom identifier and the last atom identifier.

15. The computer-readable media of claim 13, the operations further comprising:
- identifying each atom and each bond of the chemical structure of the molecule;
- identifying the scaffold of the chemical structure;
- identifying each decoration that is attached to an atom of the scaffold;
- identifying each bond between each decoration and corresponding atom of the scaffold; and
- breaking the identified bond between each decoration and corresponding atom of the scaffold.

16. The computer-readable media of claim 15, the operations further comprising:
- replacing each broken bond with a scaffold node linked to the corresponding atom of the scaffold; and
- replacing each broken bond with a decoration node lined to each decoration.

17. The computer-readable media of claim 16, the operations further comprising:
- constructing a line notation of the scaffold having a decoration marker for each decoration node; and
- constructing a line notation of each decoration.

18. The computer-readable media of claim 16, the operations further comprising:
- determining an order of the at least one decoration marker in the line notation of the scaffold; and
- arranging the at least one decoration in a decoration sequence having the order of the at least one decoration marker in the line notation of the scaffold, wherein each decoration has the decoration line notation and is separated by a decoration separator.

19. The computer-readable media of claim 13, the operations further comprising:
- arranging the scaffold sequence so that the first decoration marker precedes the first linking atom identifier of the scaffold sequence.

20. The computer-readable media of claim 13, the operations further comprising arranging the line notation to include:
- at least a subsequent decoration marker adjacent with the subsequent atom identifier;
- at least a subsequent decoration separator following the first decoration; and
- at least a subsequent decoration following the at least one subsequent decoration separator, wherein each subsequent decoration is separated by a subsequent decoration marker.

21. The computer-readable media of claim 13, the operations further comprising arranging the line notation to include:
- a plurality of decoration markers adjacent with the corresponding atom identifier;
- a plurality of decoration separators separated by a plurality of decorations; and
- each of the plurality of decorations following a corresponding decoration separator.

22. The computer-readable media of claim 13, the operations further comprising defining each decoration to include a corresponding decoration marker followed by a line notation of the chemical structure of the decoration.

23. The computer-readable media of claim 13, the operations further comprising at least one of:
- each atom identifier is defined by the periodic table;
- each decoration marker is a symbol;
- each decoration separator is a second symbol different from the decoration maker symbol; or
- each decoration marker in the scaffold sequence is bound by a third symbol that is different from the decoration maker symbol and the decoration separator symbol.

24. The non-transitory computer-readable media of claim 12, the operations further comprising:
- providing the scaffold-oriented line notation to a machine learning model as training data.

25. A computer program product comprising:
- a non-transient, tangible memory device having computer-executable instructions that when executed by a processor, cause performance of the method operations of claim 12.

26. The non-transitory computer-readable media of claim 12, the operations further comprising:
- providing the scaffold-oriented line notation for the chemical structure obtained by performing the operations of claim 12 into a computing system; and
- performing a computation protocol including at least one of a genetic algorithm, Bayesian optimization, and random search with the scaffold-oriented line notation with the computing system.

27. The non-transitory computer-readable media of claim 12, the operations further comprising:
- training a machine learning model with the scaffold-oriented line notation of the chemical structure; and
- performing a chemical analysis with the trained machine learning model.

28. The non-transitory computer-readable media of claim 27, the operations further comprising:
- designing a generated chemical structure with the trained machine learning model; and
- providing the generated chemical structure.

29. The non-transitory computer-readable media of claim 27, the operations further comprising:
- determining a desired property of the chemical structure with the trained machine learning model;
- generating a generated molecule with the trained machine learning model, wherein the generated molecule has the desired property; and
- outputting the generated molecule.

30. The non-transitory computer-readable media of claim 27, the operations further comprising generating analogs of the chemical structure used to train the machine learning model by:
- identifying at least one decoration on the chemical structure to be swapped with a different at least one decoration;
- modifying the chemical structure with the different at least one decoration to generate an analog of the chemical structure; and
- providing the analog of the chemical structure.

31. The non-transitory computer-readable media of claim 1, the operations further comprising:
- providing the scaffold-oriented line notation for the chemical structure into a computing system; and
- performing a computation protocol with the scaffold-oriented line notation with the computing system.

32. The non-transitory computer-readable media of claim 31, the operations further comprising:
- training a machine learning model with the scaffold-oriented line notation of the chemical structure; and
- performing a chemical analysis with the trained machine learning model.

33. The non-transitory computer-readable media of claim 32, the operations further comprising:
- designing a generated chemical structure with the trained machine learning model; and
- providing the generated chemical structure.

34. The non-transitory computer-readable media of claim 32, the operations further comprising:
    determining a desired property of the chemical structure with the trained machine learning model;
    generating a generated molecule with the trained machine learning model, wherein the generated molecule has the desired property; and
    outputting the generated molecule.

35. The non-transitory computer-readable media of claim 32, the operations further comprising generating analogs of the chemical structure used to train the machine learning model by:
    identifying at least one decoration on the chemical structure to be swapped with a different at least one decoration;
    modifying the chemical structure with the different at least one decoration to generate an analog of the chemical structure; and
    providing the analog of the chemical structure.

36. The non-transitory computer-readable media of claim 1, the operations further comprising:
    providing the scaffold-oriented line notation for the chemical structure into a computing system; and
    performing a computation protocol including at least one of a genetic algorithm, Bayesian optimization, and random search with the scaffold-oriented line notation with the computing system.

\* \* \* \* \*